US011464717B2

(12) United States Patent
Wenk et al.

(10) Patent No.: US 11,464,717 B2
(45) Date of Patent: Oct. 11, 2022

(54) ORAL CARE COMPOSITION CONTAINING AT LEAST ONE BIOSURFACTANT AND FLUORIDE

(71) Applicant: Evonik Degussa GmbH, Essen (DE)

(72) Inventors: Hans Henning Wenk, Mülheim an der Ruhr (DE); Kathrin Daniela Brandt, Düsseldorf (DE); Martin Schilling, Bonn (DE); Verena Dahl, Bergisch Gladbach (DE); Jochen Kleinen, Heinsberg (DE); Joachim Venzmer, Essen (DE)

(73) Assignee: Evonik Operations GmbH, Essen (DE)

( * ) Notice: Subject to any disclaimer, the term of this patent is extended or adjusted under 35 U.S.C. 154(b) by 21 days.

(21) Appl. No.: 16/470,411

(22) PCT Filed: Jan. 31, 2018

(86) PCT No.: PCT/EP2018/052335
§ 371 (c)(1),
(2) Date: Jun. 17, 2019

(87) PCT Pub. No.: WO2018/145966
PCT Pub. Date: Aug. 16, 2018

(65) Prior Publication Data
US 2019/0307657 A1    Oct. 10, 2019

(30) Foreign Application Priority Data

Feb. 10, 2017  (EP) .................................... 17155558

(51) Int. Cl.
| | | |
|---|---|---|
| *A61K 8/21* | (2006.01) | |
| *A61K 8/60* | (2006.01) | |
| *A61K 8/73* | (2006.01) | |
| *A61Q 11/00* | (2006.01) | |

(52) U.S. Cl.
CPC ................ *A61K 8/21* (2013.01); *A61K 8/602* (2013.01); *A61K 8/731* (2013.01); *A61Q 11/00* (2013.01)

(58) Field of Classification Search
CPC .......... A61K 8/21; A61K 8/602; A61K 8/731; A61Q 11/00
See application file for complete search history.

(56) References Cited

U.S. PATENT DOCUMENTS

| | | |
|---|---|---|
| 3,070,510 A | 12/1962 | Cooley et al. |
| 3,538,230 A | 11/1970 | Pader et al. |
| 3,862,307 A | 1/1975 | Di Giulio |
| 4,305,961 A | 12/1981 | Tsutsumi et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,716,601 A | 2/1998 | Rice |
| 6,051,552 A | 4/2000 | Reid et al. |
| 6,942,849 B2 | 9/2005 | Neeser et al. |
| 7,491,386 B2 | 2/2009 | Comelli et al. |
| 7,556,654 B1 | 7/2009 | Nero |
| 7,985,722 B2 | 7/2011 | Desanto |
| 8,911,982 B2 | 12/2014 | Schaffer et al. |
| 9,068,211 B2 | 6/2015 | Schaffer et al. |
| 9,085,787 B2 | 7/2015 | Schaffer et al. |
| 9,102,968 B2 | 8/2015 | Schaffer et al. |
| 9,157,108 B2 | 10/2015 | Schaffer et al. |
| 9,243,212 B2 | 1/2016 | Kuppert et al. |
| 9,271,908 B2 | 3/2016 | Allef et al. |
| 9,351,485 B2 | 5/2016 | Giessler-Blank et al. |
| 9,434,755 B2 | 9/2016 | Schilling et al. |
| 10,023,679 B2 | 7/2018 | Klostermann et al. |
| 10,292,924 B2 | 5/2019 | Schilling et al. |
| 10,292,925 B2 | 5/2019 | Gu et al. |
| 2003/0170184 A1 | 9/2003 | Comelli et al. |
| 2003/0206874 A1* | 11/2003 | Doyle ................. A61K 8/4926 424/49 |
| 2004/0171512 A1 | 9/2004 | Furuta et al. |
| 2005/0186148 A1 | 8/2005 | Neeser et al. |
| 2005/0238590 A1 | 10/2005 | Neeser et al. |
| 2008/0213194 A1 | 9/2008 | Desanto |
| 2013/0189199 A1* | 7/2013 | Pfirrmann ............... A61Q 11/00 424/52 |
| 2016/0249604 A1 | 9/2016 | Giessler-Blank et al. |
| 2016/0272667 A1* | 9/2016 | Lohitharn ................. A61L 2/18 |
| 2016/0309715 A1* | 10/2016 | Diaz de Rienzo ....... C11D 1/04 |
| 2016/0324747 A1* | 11/2016 | Ito .......................... A61K 31/27 |
| 2017/0020137 A1 | 1/2017 | Reilly |
| 2017/0202770 A1 | 7/2017 | Friedrich et al. |

(Continued)

FOREIGN PATENT DOCUMENTS

| | | |
|---|---|---|
| CA | 2 378 557 A1 | 2/2001 |
| CA | 2 410 591 A1 | 12/2001 |

(Continued)

OTHER PUBLICATIONS

Das et al., Biosurfactant from marine actinobacteria and its application in cosmetic formulation of toothpaste, Der Pharmacia Lettre 5(5):1-6 • Dec. 2013 (Year: 2013).*
Eckstein et al., United States U.S. Appl. No. 16/355,981, filed Mar. 18, 2019.
International Search Report dated Jun. 7, 2018 in PCT/EP2018/052335 (3 pages).
Klostermann et al., U.S. Appl. No. 16/315,744, filed Jan. 7, 2019.
Schilling et al., U.S. Appl. No. 16/332,979, filed Mar. 13, 2019.
Written Opinion dated Jun. 7, 2018 in PCT/EP2018/052335 (5 pages).
European Patent Convention communication dated Jul. 8, 2020 in EP 18 705 330.1 (5 pages).

(Continued)

*Primary Examiner* — Gollamudi S Kishore
(74) *Attorney, Agent, or Firm* — Taylor English Duma LLP; Philip P. McCann

(57) ABSTRACT

The present invention relates to oral care compositions comprising at least one biosurfactant and fluoride.

20 Claims, No Drawings

(56) References Cited

U.S. PATENT DOCUMENTS

| | | |
|---|---|---|
| 2017/0218120 A1 | 8/2017 | Brandt et al. |
| 2017/0306264 A1 | 10/2017 | Peggau et al. |
| 2017/0335238 A1 | 11/2017 | Schilling et al. |
| 2018/0016525 A1 | 1/2018 | Scheuermann et al. |
| 2018/0023040 A1 | 1/2018 | Schilling et al. |
| 2018/0133133 A1 | 5/2018 | Kleinen et al. |
| 2018/0179655 A1 | 6/2018 | Bauer et al. |
| 2018/0327563 A1 | 11/2018 | Klostermann et al. |
| 2018/0344602 A1 | 12/2018 | Schuch |
| 2019/0040095 A1 | 2/2019 | Lu et al. |
| 2019/0135734 A1 | 5/2019 | Liebig et al. |
| 2019/0256542 A1 | 8/2019 | Lu et al. |
| 2019/0269158 A1 | 9/2019 | Schilling et al. |

FOREIGN PATENT DOCUMENTS

| | | |
|---|---|---|
| CN | 1337439 A | 2/2002 |
| CN | 1444469 A | 9/2003 |
| DE | 2939519 A1 | 4/1980 |
| DE | 19600743 A1 | 7/1997 |
| DE | 19648439 A1 | 5/1998 |
| EP | 0 499 434 A1 | 8/1992 |
| EP | 1445302 A1 | 8/2004 |
| EP | 1411111 B1 | 9/2008 |
| EP | 2501813 A2 | 9/2012 |
| EP | 2786742 A1 | 10/2014 |
| EP | 2786743 A1 | 10/2014 |
| FR | 2740779 A1 | 5/1997 |
| FR | 2855752 A1 | 12/2004 |
| JP | S60 183032 | 9/1985 |
| JP | H01 304034 A | 12/1989 |
| JP | 2006 070231 A | 3/2006 |
| JP | 2006 083238 A | 3/2006 |
| JP | 2006 274233 A | 10/2006 |
| JP | 2007 181789 A | 7/2007 |
| JP | 2008 062179 A | 3/2008 |
| KR | 2004033376 | 3/2018 |
| WO | 01/91711 A1 | 12/2001 |
| WO | 03/002700 A1 | 1/2003 |
| WO | 03/006146 A1 | 1/2003 |
| WO | 2011/061032 A2 | 5/2011 |
| WO | 2018/145966 A1 | 8/2018 |

OTHER PUBLICATIONS

Das et al., "Biosurfactant from marine actinobacteria and its application in cosmetic formulation of toothpaste," School of Bio Sciences and Technology, VIT University, Vellore, Tamil Nadu, India, copyright 2013, Der Pharmacia Lettre, 5(5): 1-6 (6 pages).

* cited by examiner

ORAL CARE COMPOSITION CONTAINING AT LEAST ONE BIOSURFACTANT AND FLUORIDE

CROSS REFERENCE TO RELATED APPLICATIONS

This application is a 35 U.S.C. § 371 U.S. national phase entry of International Application No. PCT/EP2018/052335 having an international filing date of Jan. 31, 2018, which claims the benefit of European Application No. 17155558.4 filed Feb. 10, 2017, each of which is incorporated herein by reference in its entirety.

FIELD

The present invention relates to oral care compositions comprising at least one biosurfactant and fluoride.

BACKGROUND

The fluoride ion has been widely used topically in the treatment of dental caries for its anticariogenic and antimicrobial properties.

The mechanisms suggested for the antimicrobial and remineralization roles of fluoride for oral health include:
- reduction in demineralization by inhibition of microbial growth and metabolism
- promotion of remineralization and the formation of the fluorapatite mineral phase $(Ca_{10}(PO_4)_6F_2)$ which is, compared to hydroxyapatite $(Ca_{10}(PO_4)_6(OH)_2)$, more resistant to demineralization and acid dissolution following acid production by bacteria
- enzyme inhibition such as reduction of IgA protease synthesis
- reduction in extracellular polysaccharide production which helps in decreasing bacterial adherence to dental hard tissues.

Fluoride is added into toothpastes mostly as sodium fluoride (NaF), sodium monofluorophosphate (MFP), amine fluoride, and stannous fluoride. The other ingredients of toothpaste may also affect the availability of fluoride in the oral cavity. This is especially true in the case of calcium containing abrasives due to their potential to inactivate the fluoride.

Similarly, fluoride will react with silica to form fluorosilicates if a sufficient amount of detergent is not present.

Stannous fluoride gels (0.4% $SnF_2$, equivalent to 970 ppm of fluoride) are effective in arresting root surface caries and have been incorporated into artificial saliva to reduce caries after radiation therapy in cancer patients. Stannous fluoride gel has a bad taste and may stain the teeth.

SUMMARY

Thus, there is a need for improved oral care compositions such as toothpastes, mouth rinses, gels, varnishes etc. containing fluoride.

DETAILED DESCRIPTION

Surprisingly, it has been found that the oral care compositions described below containing biosurfactant and fluoride are able to solve the problem addressed by the invention.

An advantage of the present invention is that the compositions bear a reduced formation of insoluble complexes of fluoride with for example calcium.

A further advantage of the present invention is that the compositions induce a reduced staining of teeth.

A further advantage of the present invention is an improved taste of the compositions.

A further advantage of the invention is that the compositions have an improved deposition/retention of fluoride on surfaces.

A further advantage of the present invention is that the compositions reduce dental plaque.

A further advantage of the present invention is that the compositions reduce oral malodor.

The present invention relates to oral care compositions containing at least one biosurfactant and at least one fluoride ion source.

Within the context of the present invention, "biosurfactant" is understood to mean any glycolipid produced by fermentation.

Unless otherwise stated, all percentages (%) given are percentages by weight.

The oral care compositions can be present in various different forms, including a dentifrice, paste, gel, medicament, powder, mouthrinse, mouthwash, tooth hardener, oral film, slurry, injectable solution, chewing gum and lozenge, as well as any other form of oral care compositions known in the art.

In a preferred embodiment, the composition according to the invention is characterized in that the biosurfactant is selected from the group consisting of rhamnolipids, sophorolipids, glucose lipids, cellulose lipids and trehalose lipids, preferably rhamnolipids and sophorolipids with rhamnolipids being the most preferred.

The biosurfactants, in particular glycolipid surfactants, can be produced e.g. as in EP 0 499 434, U.S. Pat. No. 7,985,722, WO 03/006146, JP 60 183032, DE 19648439, DE 19600743, JP 01 304034, CN 1337439, JP 2006 274233, KR 2004033376, JP 2006 083238, JP 2006 070231, WO 03/002700, FR 2740779, DE 2939519, U.S. Pat. No. 7,556,654, FR 2855752, EP 1445302, JP 2008 062179 and JP 2007 181789 or the documents cited therein. Suitable biosurfactants can be acquired e.g. from Soliance, France and Evonik Industries AG, Germany.

The composition according to the invention preferably has, as biosurfactants, rhamnolipids, in particular mono-, di- or polyrhamnolipids, and/or sophorolipids.

The composition according to the invention particularly preferably has, as biosurfactants, one or more of the sophorolipids described in EP2501813 with the formulae (Ia) and (Ib).

Sophorolipids can be used according to the invention in their acid form or in their lactone form. The term "acid form" of sophorolipids refers to the general formula (Ia) of EP2501813; the term "lactone form" of sophorolipids refers to the general formula (Ib) of EP2501813.

For the determination of the content of sophorolipids in the acid or lactone form in a composition, reference is made to EP1411111B1, page 8, paragraph [0053].

Preferred compositions according to the invention comprise as biosurfactant a sophorolipid in which the weight ratio of lactone form to the acid form is in the range from 20-80 to 80-20, most preferably in the ranges from 30-70 to 40-60.

The term "rhamnolipid" in the context of the present invention is understood to mean particularly compounds of the general formula (I) or salts thereof,

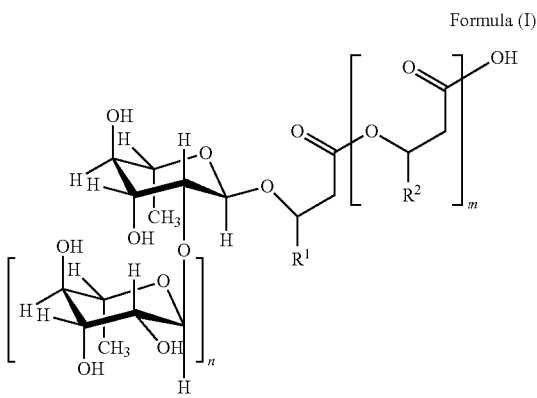

Formula (I)

where
m=2, 1 or 0, in particular 1,
n=1 or 0,
$R^1$ and $R^2$=mutually independently, identical or different, organic radical having 2 to 24, preferably 5 to 13 carbon atoms, in particular optionally branched, optionally substituted, particularly hydroxy-substituted, optionally unsaturated, in particular optionally mono-, bi- or tri-unsaturated alkyl radical, preferably those selected from the group consisting of pentenyl, heptenyl, nonenyl, undecenyl and tridecenyl and $(CH_2)_o$—$CH_3$ where o=1 to 23, preferably 4 to 12.

The term "di-rhamnolipid" in the context of the present invention is understood to mean compounds of the general formula (I) or salts thereof, where n=1.

The term "mono-rhamnolipid" in the context of the present invention is understood to mean compounds of the general formula (I) or salts thereof, where n=0.

Distinct rhamnolipids are abbreviated according to the following nomenclature: "diRL-CXCY" is understood to mean di-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

"monoRL-CXCY" is understood to mean mono-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used therefore does not distinguish between "CXCY" and "CYCX".

For rhamnolipids where m=0, monoRL-CX or diRL-CX is used accordingly.

If one of the abovementioned indices X and/or Y is provided with ":Z", this signifies that the respective radical $R^1$ and/or $R^2$ is equal to an unbranched, unsubstituted hydrocarbon radical having X-3 or Y-3 carbon atoms having Z double bonds.

To determine the content of rhamnolipids in the context of the present invention, only the mass of the rhamnolipid anion is considered, i.e. "general formula (I) less one hydrogen".

To determine the content of rhamnolipids in the context of the present invention, all rhamnolipids are converted by acidification into the protonated form (cf. general formula (I)) and quantified by HPLC.

A composition preferred according to the invention is characterized in that it comprises a mixture of rhamnolipids, where the weight ratio of di-rhamnolipids to mono-rhamnolipids in the mixture is greater than 51:49, preferably greater than 75:25, particularly preferably greater 90:10, particularly preferably greater 97:3 particularly preferably greater than 98:2.

A composition preferred according to the invention is characterized in that the rhamnolipid mixture comprises 51% by weight to 95% by weight, preferably 70% by weight to 90% by weight, particularly preferably 75% by weight to 85% by weight, of diRL-C10C10 and 0.5% by weight to 9% by weight, preferably 0.5% by weight to 3% by weight, particularly preferably 0.5% by weight to 2% by weight, of monoRL-C10C10, where the percentages by weight refer to the sum total of all rhamnolipids present.

A composition preferred according to the invention is characterized in that the rhamnolipid mixture, in addition to the diRL-C10C10 and monoRL-C10C10 contents mentioned above, comprises
0.5% by weight to 15% by weight, preferably 3% by weight to 12% by weight, particularly preferably 5% by weight to 10% by weight, of diRL-C10C12:1,
where the percentages by weight refer to the sum total of all rhamnolipids present.

A composition preferred according to the invention is characterized in that the rhamnolipid mixture, in addition to the diRL-C10C10 and monoRL-C10C10 contents mentioned above, comprises 0.1% by weight to 5% by weight, preferably 0.5% by weight to 3% by weight, particularly preferably 0.5% by weight to 2% by weight, of monoRL-C10C12 and/or, preferably and 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

It can be advantageous and is therefore preferred if the rhamnolipid mixture present in the composition according to the invention, in addition to the diRL-C10C10 and monoRL-C10C10 contents mentioned above, comprises 0.1% by weight to 25% by weight, preferably 2% by weight to 10% by weight, particularly preferably 4% by weight to 8% by weight, of diRL-C8C10, where the percentages by weight refer to the sum total of all rhamnolipids present.

The composition according to the invention preferably has, the fluoride ion source selected from the group consisting of stannous fluoride, sodium fluoride, potassium fluoride, potassium monofluorophosphate, sodium monofluorophosphate, ammonium monofluorophosphate, sodium fluorosilicate, ammonium fluorosilicate, amine fluorides such as olaflur (N'-octadecyltrimethylendiamine-N,N,N'-tris (2-ethanol)-dihydrofluoride) and ammonium fluoride.

The fluoride ion source is preferably contained in the composition according to the invention in an amount sufficient to supply 50 to 25000 ppm fluoride ion, e.g., from 100 to 1000, from 200 to 500, or 250 ppm fluoride ion %, based on the total weight of the composition. Fluoride ion sources may be added to the compositions of the invention at a level of 0.001 wt. % to 10 wt. %, e.g., from 0.003 wt. % to 5 wt. %, 0.01 wt. % to 1 wt., or 0.05 wt. %, based on the total weight of the composition. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The composition according to the invention preferably is characterized in that the biosurfactant is contained in an amount from 0.005 wt. % to 20 wt. %, preferably 0.1 wt. % to 10 wt. %, more preferably 0.5 wt % to 5 wt % and particular preferably from 0.1 wt. % to 2 wt. % based on the total weight of the composition.

The fluoride ion source should provide from about 50 ppm to about 25000 ppm, preferably from about 50 ppm to 2500 ppm fluoride, particular preferably from about 50 ppm to 250 ppm for mouthrinses and from about 250 ppm to about 1500 ppm for toothpastes and gels. Particularly preferred compositions according to the invention are characterized in that the biosurfactant is selected from the group consisting of rhamnolipids in an amount from 0.1 wt. % to 2 wt. %, and the fluoride ion source is contained in an amount sufficient to supply from 50 ppm to 1500 ppm fluoride ion.

Particularly preferred compositions according to the invention are characterized in that they are selected from toothpastes and gels, and that the biosurfactant is selected from the group consisting of rhamnolipids in an amount from 0.1 wt. % to 2 wt. %, and the fluoride ion source is contained in an amount sufficient to supply from 500 ppm to 1500 ppm ppm fluoride ion. Particularly preferred compositions according to the invention are characterized in that they are selected from mouthrinses, and that the biosurfactant is selected from the group consisting of rhamnolipids in an amount from 0.1 wt. % to 2 wt. %, and the fluoride ion source is contained in an amount sufficient to supply from 50 ppm to 250 ppm fluoride ion.

The oral care compositions may be provided in an orally acceptable carrier or vehicle. The carrier can be a liquid, semi-solid, or solid phase, in the form of a mouth rinse, dentifrice (including toothpastes, toothpowders, and prophylaxis pastes), confectionaries (including lozenges, and gum), medicament, film, or any other form known to one of skill in the art. Selection of specific carrier components is dependent on the desired product form.

In embodiments where the oral care composition is in the form of a mouthrinse, an exemplary carrier is substantially liquid. The term "mouthrinse" includes mouthwashes, sprays and the like. In such a composition the orally acceptable carrier typically has an aqueous phase comprising either water, or a water and alcohol, preferably ethanol, mixture.

The oral care compositions of the present invention may further comprise additional ingredients. These additional ingredients may include, but are not limited to, diluents, bicarbonate salts, surfactants, foam modulators, sweeteners, flavorants, pigments, colorants, antibacterial agents, anticaries agents, anticalculus, tooth whitening agents, coolants or tartar control agents, and mixtures thereof.

An abrasive polishing material may also be included in the oral care compositions according to the present invention. The abrasive polishing material contemplated for use in the compositions of the present invention can be any material which does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed in U.S. Pat. No. 3,070,510. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in U.S. Pat. Nos. 3,538,230 and 3,862,307. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in U.S. Pat. No. 4,340,583. Silica abrasives are also described in U.S. Pat. Nos. 5,589,160, 5,603,920, 5,651,958, 5,658,553 and 5,716,601. The abrasive in the toothpaste compositions described herein is generally present at a level of from about 6% to about 70% by weight of the composition. Preferably, toothpastes contain from about 10% to about 50% of abrasive, by weight of the dentifrice composition.

In some embodiments, the compositions of the present invention also comprise an antibacterial or preservative agent, such as benzyl alcohol, chlorhexidine digluconate, triclosan, benzalkonium chloride, cetyl pyridinium chloride or parabens such as methylparaben or propylparaben. In some embodiments, the preservative is benzyl alcohol. The antibacterial or preservative agent may be present in the composition in an amount of from 0.1 to 1 weight %; 0.2 to 0.5 weight %; or about 0.3 weight % by total weight of the composition.

In some embodiments, the oral care compositions further comprise a humectant. In certain embodiments, the humectant is selected from sorbitol, glycerin, xylitol, polyethylene glycol, propylene glycol, and combinations thereof. In some embodiments, the humectant is glycerin. In some embodiments, the humectant is sorbitol, In certain embodiments, the humectant is present in the composition in an amount of from 5 to 20 weight %; from 7 to 17 weight %; or from 8 to 13 weight %; or from 9 to 10 weight %, based on the total weight of the composition. When the humectant is supplied as a solution in water, for example sorbitol as a 70 weight % solution in water, the amount of humectant is calculated as the active weight of the humectant, e.g. for a composition comprising 25 weight % sorbitol (as 70 weight % aqueous solution), the concentration of humectant is 17.5 weight %.

In some embodiments, the composition has a pH of from 3.5 to 10.5, preferably from 8.5 to 10.5; or from 9.2 to 10.2. The "pH" in connection with the present invention is defined as the value which is measured for the relevant substance at 25° C. after stirring for 5 minutes using a pH electrode calibrated in accordance with ISO 4319 (1977).

In certain embodiments, the composition comprises a buffer system, which may be: (a) a combination of sodium silicate and tetrasodium pyrophosphate; (b) a combination of sodium hydroxide, sodium bicarbonate and tetrasodium pyrophosphate; or (c) a combination of sodium bicarbonate and sodium carbonate.

In some embodiments, the buffer system is 0.04 to 0.5 weight % sodium hydroxide, 0.25 to 0.75 weight % sodium bicarbonate and 0.25 to 1.5 weight % tetrasodium pyrophosphate; or about 0.12 weight % sodium hydroxide, about 0.25 weight % sodium bicarbonate and about 1.25 weight % tetrasodium pyrophosphate; or about 0.06 weight % sodium hydroxide, about 0.5 weight % sodium bicarbonate and about 0.5 weight % tetrasodium pyrophosphate based on the total weight of the composition. In some embodiments, the buffer system is 0.05 to 0.5 weight % sodium bicarbonate and 0.2 to 0.6 weight % sodium carbonate; or about 0.1 weight % sodium bicarbonate and 0.4 weight % sodium carbonate, based on the total weight of the composition.

In some embodiments, the oral care compositions of the present invention comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

The oral care compositions of the invention may also comprise at least one polymeric viscosity modifier. Suitable polymeric viscosity modifiers include cellulose derivatives ("cellulose gums") such as carboxymethyl cellulose (CMC), methyl cellulose, hydroxyethyl cellulose, hydroxypropyl methyl cellulose, and mixtures thereof; polyvinyl pyrrolidone; xanthan; carrageenans such as iota-carrageenan, kappa-carrageenan, kappa2-carrageenan, lambda-carrageenan, and mixtures thereof; guar gum; gum karaya; gum arabic; gum tragacanth; and mixtures thereof. Other suitable polymeric viscosity modifiers include Carbomer 910, Carbomer 934, Carbomer 940, and Carbomer 980 and similar polymers of acrylic acid which are cross-linked with polyalcohol allyl ethers.

The oral care compositions of the invention may also comprise at least one further (non-bio-) surfactant. Any orally acceptable surfactant, most of which are anionic, nonionic or amphoteric, can be used. Suitable anionic surfactants include without limitation, water-soluble salts of C8-20 alkyl sulfates, sulfonated monoglycerides of C8-20 fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of C8-20 aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

The oral care compositions of the invention may comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000 000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

The oral care compositions of the present invention may comprise at least one sweetener (such as, for example, sodium saccharin), useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions of the present invention may also comprise at least one flavorant, useful for example to enhance taste of the composition. Any orally acceptable natural or synthetic flavorant can be used, including without limitation tea flavors, vanillin, sage, marjoram, parsley oil, spearmint oil, cinnamon oil, oil of wintergreen (methylsalicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, *eucalyptus* oil, eucalyptol, anethole, eugenol, *cassia*, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the composition.

The compositions of the present invention may comprise at least one colorant. Colorants herein include pigments, dyes, lakes and agents imparting a particular luster or reflectivity such as pearling agents. Any orally acceptable colorant can be used, including without limitation titanium dioxide, zinc oxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

The compositions of the present invention may comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention may include antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof.

Such agents may be added in effective amounts, e.g., from about 1 wt. % to about 20 wt. % by weight based on the total weight of the composition, depending on the agent chosen.

The composition of the present invention may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention may additionally optionally comprise a tartar control (anticalculus) agent as provided below. Tartar control agents among those useful herein include salts of the specified agents, including alkali metal and ammonium salts. The agents include: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

The composition of the invention may further comprise enzymes, including endoglycosidase, papain, dextranase, mutanase, amyloglucosidase, glucose oxidase, lysozyme, lactoperoxidase, and mixtures thereof.

The present invention further relates to the use of biosurfactants selected from the group consisting of rhamnolipids, sophorolipids, glucose lipids, cellulose lipids and trehalose lipids, preferably rhamnolipids and/or sophorolipids, particularly preferred rhamnolipids, for a reduced formation of insoluble complexes of fluoride, preferably with calcium.

The present invention further relates to the use of biosurfactants selected from the group consisting of rhamnolipids, sophorolipids, glucose lipids, cellulose lipids and trehalose lipids, preferably rhamnolipids and/or sophorolipids, particularly preferred rhamnolipids, for a reduced staining of teeth.

The present invention further relates to the use of biosurfactants selected from the group consisting of rhamnolipids, sophorolipids, glucose lipids, cellulose lipids and trehalose lipids, preferably rhamnolipids and/or sophorolipids, particularly preferred rhamnolipids, for an improved deposition/retention of fluoride on surfaces, especially teeth.

Preferred use according to the invention uses the preferred oral care compositions mentioned above.

The examples adduced below illustrate the present invention by way of example, without any intention of restricting the invention, the scope of application of which is apparent from the entirety of the description and the claims, to the embodiments specified in the examples.

EXAMPLES

In all examples, a mixture of rhamnolipids as listed below was used:

| RL total [%] (HPLC) | 91 |
| --- | --- |
| diRL-C8C10 | 13.9 |
| monoRL-C8C10 | 0.51 |
| diRL-C10C10 | 61.4 |
| monoRL-C10C10 | 1.4 |
| diRL-C10C12:1 | 5.9 |
| diRL-C10C12 | 5.5 |
| other RL | 2.2 |

Example 1a: Reduced Oral Malodor after Smoking

The first example demonstrates that the combination of Rhamnolipid and Fluoride reduces oral malodor caused by cigarette smoking.

The breath of 24 smokers was evaluated on the basis of a sensory analysis performed by a trained panel of ten experts. The group of 24 smokers was subdivided into three subgroups, 1, 2, and 3, of 8 smokers each. The smokers rinsed their mouth with 20 ml of mouth rinse A (subgroup 1), B (subgroup 2) or C (subgroup 3) for 30 seconds.

The mouth rinse formulations are described in table A:

TABLE A

Mouth rinse formulations

| Raw materials (% w/w) | Mouth rinse formulation A (not according to the invention) | Mouth rinse formulation B (not according to the invention) | Mouth rinse formulation C (according to the invention) |
| --- | --- | --- | --- |
| Ethylalcohol | 10.00 | 10.00 | 10.00 |
| PEG-40 Hydrogenated Castor Oil | 1.50 | — | — |
| Rhamnolipid | — | 1.50 | 1.50 |
| Benzoic Acid | 0.12 | 0.12 | 0.12 |
| Flavor | 0.15 | 0.15 | 0.15 |
| Water demin. | ad 100 | ad 100 | ad 100 |
| Sorbitol 70% | 5.00 | 5.00 | 5.00 |
| Sodium-saccharin 450 | 0.07 | 0.07 | 0.07 |
| Sodium Fluoride | 0.05 | — | 0.05 |

Approximately two hours after mouth rinsing they smoked a cigarette (Marlboro brand). Five minutes after smoking the breath of the smokers was evaluated by the trained experts on a scale from 1 (strong smoker breath) to 3 (no smoker breath).

The results of the sensory analysis are depicted in table B:

TABLE B

Results of the sniff analysis after cigarette smoking

| | Mouth rinse formulation A (not according to the invention) | Mouth rinse formulation B (not according to the invention) | Mouth rinse formulation C (according to the invention) |
| --- | --- | --- | --- |
| Scoring 5 min after smoking; mean values | 1.4 | 1.6 | 2.7 |

Notably, the malodor after cigarette smoking was significantly reduced when the smokers rinsed their mouths with a mouth rinse comprising both Rhamnolipid and Fluoride prior to smoking.

Example 1b: Reduced Oral Malodor after Smoking

In an additional test the breath of 24 smokers was evaluated on the basis of a sensory analysis performed by a trained panel of ten experts. The group of 24 smokers was subdivided into three subgroups, 1, 2, and 3, of 8 smokers each. The smokers rinsed their mouth with 20 ml of mouth rinse A (subgroup 1), B (subgroup 2) or C (subgroup 3) for 30 seconds.

The mouth rinse formulations are described in table C:

TABLE C

Mouth rinse formulations

| Raw materials (% w/w) | Mouth rinse formulation D (not according to the invention) | Mouth rinse formulation E (not according to the invention) | Mouth rinse formulation F (according to the invention) |
|---|---|---|---|
| Ethylalcohol | 10.00 | 10.00 | 10.00 |
| PEG-40 Hydrogenated Castor Oil | 3.00 | — | — |
| Sophorolipid | — | 3.00 | 3.00 |
| Benzoic Acid | 0.12 | 0.12 | 0.12 |
| Flavor | 0.15 | 0.15 | 0.15 |
| Water demin. | ad 100 | ad 100 | ad 100 |
| Sorbitol 70% | 5.00 | 5.00 | 5.00 |
| Sodium-saccharin 450 | 0.07 | 0.07 | 0.07 |
| Sodium Fluoride | 0.05 | — | 0.05 |

Approximately two hours after mouth rinsing they smoked a cigarette (Marlboro brand). Five minutes after smoking the breath of the smokers was evaluated by the trained experts on a scale from 1 (strong smoker breath) to 3 (no smoker breath).

The results of the sensory analysis are depicted in table D:

TABLE D

Results of the sniff analysis after cigarette smoking

| | Mouth rinse formulation D (not according to the invention) | Mouth rinse formulation E (not according to the invention) | Mouth rinse formulation F (according to the invention) |
|---|---|---|---|
| Scoring 5 min after smoking; mean values | 1.2 | 1.3 | 2.4 |

Notably, the malodor after cigarette smoking was significantly reduced when the smokers rinsed their mouths with a mouth rinse comprising both Sophorolipid and Fluoride prior to smoking.

Example 1c: Reduced Oral Malodor after Smoking

In an additional test the breath of 24 smokers was evaluated on the basis of a sensory analysis performed by a trained panel of ten experts. The group of 24 smokers was subdivided into three subgroups, 1, 2, and 3, of 8 smokers each. The smokers rinsed their mouth with 20 ml of mouth rinse A (subgroup 1), B (subgroup 2) or C (subgroup 3) for 30 seconds.

The mouth rinse formulations are described in table E:

TABLE E

Mouth rinse formulations

| Raw materials (% w/w) | Mouth rinse formulation G (not according to the invention) | Mouth rinse formulation H (not according to the invention) | Mouth rinse formulation I (according to the invention) |
|---|---|---|---|
| Ethylalcohol | 10.00 | 10.00 | 10.00 |
| PEG-40 Hydrogenated Castor Oil | 1.0 | — | — |
| Celluloselipid | — | 1.0 | 1.0 |
| Benzoic Acid | 0.12 | 0.12 | 0.12 |
| Flavor | 0.15 | 0.15 | 0.15 |
| Water demin. | ad 100 | ad 100 | ad 100 |
| Sorbitol 70% | 5.00 | 5.00 | 5.00 |
| Sodium-saccharin 450 | 0.07 | 0.07 | 0.07 |
| Sodium Fluoride | 0.025 | — | 0.025 |

Approximately two hours after mouth rinsing they smoked a cigarette (Marlboro brand). Five minutes after smoking the breath of the smokers was evaluated by the trained experts on a scale from 1 (strong smoker breath) to 3 (no smoker breath).

The results of the sensory analysis are depicted in table F:

TABLE F

Results of the sniff analysis after cigarette smoking

| | Mouth rinse formulation G (not according to the invention) | Mouth rinse formulation H (not according to the invention) | Mouth rinse formulation I (according to the invention) |
|---|---|---|---|
| Scoring 5 min after smoking; mean values | 1.5 | 1.6 | 2.4 |

Notably, the malodor after cigarette smoking was significantly reduced when the smokers rinsed their mouths with a mouth rinse comprising both Celluloselipid and Fluoride prior to smoking.

Example 2a: Improved Taste after Tooth Brushing

The following example demonstrates that the combination of Rhamnolipid and Fluoride reduces the bitter taste of foods and beverages after tooth brushing.

Three toothpaste formulations were compared to each other on the basis of a sensory analysis performed by a trained panel of ten experts. The study was blinded. The toothpaste formulations are described in table G:

TABLE G

Toothpaste formulations

| Raw materials (% w/w) | Toothpaste formulation A (not according to the invention) | Toothpaste formulation B (not according to the invention) | Toothpaste formulations C (according to the invention) |
|---|---|---|---|
| Hydrated Silica (Hydrated) | 22.00 | 22.00 | 22.00 |
| Sorbitol 70% | 50.00 | 50.00 | 50.00 |
| SLS | 1.50 | — | — |

TABLE G-continued

Toothpaste formulations

| Raw materials (% w/w) | Toothpaste formulation A (not according to the invention) | Toothpaste formulation B (not according to the invention) | Toothpaste formulations C (according to the invention) |
|---|---|---|---|
| Rhamnolipid | — | 1.50 | 1.50 |
| NaCMC (7MXF) | 1.20 | 1.20 | 1.20 |
| Flavor (Optamint ® #757637) | 1.0 | 1.00 | 1.00 |
| Paraffin oil | 0.50 | 0.50 | 0.50 |
| Titanium dioxide | 0.40 | 0.40 | 0.40 |
| Sodium Fluoride | 0.22 | — | 0.22 |
| Methylparabene Na-salt | 0.20 | 0.20 | 0.20 |
| Saccharine Na | 0.10 | 0.10 | 0.10 |
| Water demin. | Ad 100 | Ad 100 | Ad 100 |

The ten panelists brushed their teeth with 1 g of the respective toothpaste by means of manual toothbrushes (Dr. Best original mittel) for 3 min. Subsequently, the oral cavity was rinsed with 200 ml water. After 3 min the experts drank 20 ml orange juice (Hohes C "Milde Orange") and evaluated the taste on a scale from 1 (very bitter) to 3 (not bitter). Between testing the different toothpastes, the experts regenerated until the taste entirely vanished and at least 2 hours.

The results of the sensory analysis are depicted in table H:

TABLE H

Results of the taste analysis after tooth brushing and drinking orange juice

| | Toothpaste formulation A (not according to the invention) | Toothpaste formulation B (not according to the invention) | Toothpaste formulations C (according to the invention) |
|---|---|---|---|
| Scoring 3 min after tooth brushing; mean values | 1.1 | 1.3 | 2.5 |

Notably, the taste of orange juice was significantly less bitter after tooth brushing if the toothpaste comprises both Rhamnolipid and Fluoride.

Example 2b: Improved Taste after Tooth Brushing

The following example demonstrates that the combination of Sophorolipid and Fluoride reduces the bitter taste of foods and beverages after tooth brushing.

Three toothpaste formulations were compared to each other on the basis of a sensory analysis performed by a trained panel of ten experts. The study was blinded. The toothpaste formulations are described in table I:

TABLE I

Toothpaste formulations

| Raw materials (% w/w) | Toothpaste formulation D (not according to the invention) | Toothpaste formulation E (not according to the invention) | Toothpaste formulations F (according to the invention) |
|---|---|---|---|
| Hydrated Silica (Hydrated) | 22.00 | 22.00 | 22.00 |
| Sorbitol 70% | 50.00 | 50.00 | 50.00 |
| SLS | 1.50 | — | — |

TABLE I-continued

Toothpaste formulations

| Raw materials (% w/w) | Toothpaste formulation D (not according to the invention) | Toothpaste formulation E (not according to the invention) | Toothpaste formulations F (according to the invention) |
|---|---|---|---|
| Sophorolipid | — | 1.50 | 1.50 |
| NaCMC (7MXF) | 1.20 | 1.20 | 1.20 |
| Flavor (Optamint ® #757637) | 1.0 | 1.00 | 1.00 |
| Paraffin oil | 0.50 | 0.50 | 0.50 |
| Titanium dioxide | 0.40 | 0.40 | 0.40 |
| Sodium Fluoride | 1.00 | — | 1.00 |
| Methylparabene Na-salt | 0.20 | 0.20 | 0.20 |
| Saccharine Na | 0.10 | 0.10 | 0.10 |
| Water demin. | Ad 100 | Ad 100 | Ad 100 |

The ten panelists brushed their teeth with 1 g of the respective toothpaste by means of manual toothbrushes (Dr. Best original mittel) for 3 min. Subsequently, the oral cavity was rinsed with 200 ml water. After 3 min the experts drank 20 ml orange juice (Hohes C "Milde Orange") and evaluated the taste on a scale from 1 (very bitter) to 3 (not bitter). Between testing the different toothpastes, the experts regenerated until the taste entirely vanished and at least 2 hours.

The results of the sensory analysis are depicted in table J:

TABLE J

Results of the taste analysis after tooth brushing and drinking orange juice

| | Toothpaste formulation D (not according to the invention) | Toothpaste formulation E (not according to the invention) | Toothpaste formulations F (according to the invention) |
|---|---|---|---|
| Scoring 3 min after tooth brushing; mean values | 1.3 | 1.4 | 2.8 |

Notably, the taste of orange juice was significantly less bitter after tooth brushing if the toothpaste comprises both Sophorolipid and Fluoride.

Example 2c: Improved Taste after Tooth Brushing

The following example demonstrates that the combination of Trehaloselipid and Fluoride reduces the bitter taste of foods and beverages after tooth brushing.

Three toothpaste formulations were compared to each other on the basis of a sensory analysis performed by a trained panel of ten experts. The study was blinded. The toothpaste formulations are described in table K:

TABLE K

Toothpaste formulations

| Raw materials (% w/w) | Toothpaste formulation G (not according to the invention) | Toothpaste formulation H (not according to the invention) | Toothpaste formulations I (according to the invention) |
|---|---|---|---|
| Hydrated Silica (Hydrated) | 22.00 | 22.00 | 22.00 |
| Sorbitol 70% | 50.00 | 50.00 | 50.00 |
| SLS | 0.7 | — | — |

TABLE K-continued

Toothpaste formulations

| Raw materials (% w/w) | Toothpaste formulation G (not according to the invention) | Toothpaste formulation H (not according to the invention) | Toothpaste formulations I (according to the invention) |
|---|---|---|---|
| Trehaloselipid | — | 0.7 | 0.7 |
| NaCMC (7MXF) | 1.20 | 1.20 | 1.20 |
| Flavor (Optamint ® #757637) | 1.0 | 1.00 | 1.00 |
| Paraffin oil | 0.50 | 0.50 | 0.50 |
| Titanium dioxide | 0.40 | 0.40 | 0.40 |
| Sodium Fluoride | 0.14 | — | 0.14 |
| Methylparabene Na-salt | 0.20 | 0.20 | 0.20 |
| Saccharine Na | 0.10 | 0.10 | 0.10 |
| Water demin. | Ad 100 | Ad 100 | Ad 100 |

The ten panelists brushed their teeth with 1 g of the respective toothpaste by means of manual toothbrushes (Dr. Best original mittel) for 3 min. Subsequently, the oral cavity was rinsed with 200 ml water. After 3 min the experts drank 20 ml orange juice (Hohes C "Milde Orange") and evaluated the taste on a scale from 1 (very bitter) to 3 (not bitter). Between testing the different toothpastes, the experts regenerated until the taste entirely vanished and at least 2 hours.

The results of the sensory analysis are depicted in table L:

TABLE L

Results of the taste analysis after tooth brushing and drinking orange juice

| | Toothpaste formulation G (not according to the invention) | Toothpaste formulation H (not according to the invention) | Toothpaste formulations I (according to the invention) |
|---|---|---|---|
| Scoring 3 min after tooth brushing; mean values | 1.4 | 1.9 | 2.3 |

Notably, the taste of orange juice was significantly less bitter after tooth brushing if the toothpaste comprises both Trehaloselipid and Fluoride.

Example 3: Foam Volume of Fluoride Containing Toothpaste Formulations

The following example demonstrates that the presence of fluoride in a toothpaste formulation does not lead to a reduction in foam volume in a Rhamnolipid or Sophorolipid containing chassis formulation if Calcium is available (e.g. from water hardness), whereas the foam volume is reduced in a SLS or CAPB containing chassis formulation in the presence of calcium from water hardness.

The evaluation was conducted by means of a paired sensory comparison test for the descriptor of foam volume (blinded study, toothpaste formulation pairs randomized). Ten panelists brushed their teeth with a mixture of 5 g water and 1 g of a toothpaste containing one of the toothpastes in Table M or N by means of manual toothbrushes (Dr. Best original mittel) for 30 sec. The toothpastes were either mixed with a solution containing $CaCl_2$ (316.6 mg/L equal to 2.85 mmol/L of Ca' equal to 16° dH (German Hardness) or NaCl (166.7 mg/L equal to 2.85 mmol/L $Na^+$). Deminieralized water was used to prepare the salt solutions. After rinsing thoroughly with 200 ml of water the panelists brushed their teeth with the corresponding toothpaste from the other table in the same manner as before. The panelists were asked to compare the foam volumes of the two toothpaste formulations. Results of the paired foam tests are first presented for the tests in which the toothpaste was diluted with water containing $CaCl_2$) (Tables O, P, Q, R) and then with water containing NaCl (Tables S, T, U, V).

TABLE M

Toothpaste formulations

| Raw materials (% w/w) | Toothpaste formulation J1 (not according to the invention) | Toothpaste formulation K1 (not according to the invention) | Toothpaste formulations L1 (not according to the invention) | Toothpaste formulations M1 (not according to the invention) |
|---|---|---|---|---|
| Hydrated Silica (Hydrated) | 22.00 | 22.00 | 22.00 | 22.00 |
| Sorbitol 70% | 50.00 | 50.00 | 50.00 | 50.00 |
| SLS | 0.7 | — | — | — |
| CAPB | — | 0.7 | — | — |
| Rhamnolipid | — | — | 0.7 | — |
| Sophorolipid | — | — | — | 0.7 |
| NaCMC (7MXF) | 1.20 | 1.20 | 1.20 | 1.20 |
| Flavor (Optamint ® #757637) | 1.0 | 1.00 | 1.00 | 1.00 |
| Paraffin oil | 0.50 | 0.50 | 0.50 | 0.50 |
| Titanium dioxide | 0.40 | 0.40 | 0.40 | 0.40 |
| Sodium Fluoride | — | — | — | — |
| Methylparabene Na-salt | 0.20 | 0.20 | 0.20 | 0.20 |
| Saccharine Na | 0.10 | 0.10 | 0.10 | 0.10 |
| Water demin. | Ad 100 | Ad 100 | Ad 100 | Ad 100 |

TABLE N

Toothpaste formulations

| Raw materials (% w/w) | Toothpaste formulation J2 (not according to the invention) | Toothpaste formulation K2 (not according to the invention) | Toothpaste formulations L2 (according to the invention) | Toothpaste formulations M2 (according to the invention) |
|---|---|---|---|---|
| Hydrated Silica (Hydrated) | 22.00 | 22.00 | 22.00 | 22.00 |
| Sorbitol 70% | 50.00 | 50.00 | 50.00 | 50.00 |
| SLS | 0.7 | — | — | — |
| CAPB | — | 0.7 | — | — |
| Rhamnolipid | — | — | 0.7 | — |
| Sophorolipid | — | — | — | 0.7 |
| NaCMC (7MXF) | 1.20 | 1.20 | 1.20 | 1.20 |
| Flavor (Optamint ® #757637) | 1.0 | 1.00 | 1.00 | 1.00 |
| Paraffin oil | 0.50 | 0.50 | 0.50 | 0.50 |
| Titanium dioxide | 0.40 | 0.40 | 0.40 | 0.40 |
| Sodium Fluoride | 0.14 | 0.14 | 0.14 | 0.14 |
| Methylparabene Na-salt | 0.20 | 0.20 | 0.20 | 0.20 |
| Saccharine Na | 0.10 | 0.10 | 0.10 | 0.10 |
| Water demin. | Ad 100 | Ad 100 | Ad 100 | Ad 100 |

TABLE O

Assessment of the toothpaste formulations containing SLS in presence of $CaCl_2$ (J1, J2 not according to the invention)

| | Foam volume J1 > J2 | Foam volume J1 = J2 | Foam volume J1 < J2 |
|---|---|---|---|
| Result of the panel test, sum over all panelists | 8 | 1 | 1 |

TABLE P

Assessment of the toothpaste formulations containing CAPB in presence of $CaCl_2$ (K1, K2 not according to the invention)

| | Foam volume K1 > K2 | Foam volume K1 = K2 | Foam volume K1 < K2 |
|---|---|---|---|
| Result of the panel test, sum over all panelists | 6 | 3 | 1 |

TABLE Q

Assessment of the toothpaste formulations containing Rhamnolipid in presence of $CaCl_2$ (L1 not according to the invention, L2 according to the invention)

| | Foam volume L1 > L2 | Foam volume L1 = L2 | Foam volume L1 < L2 |
|---|---|---|---|
| Result of the panel test, sum over all panelists | 1 | 8 | 1 |

TABLE R

Assessment of the toothpaste formulations containing Sophorolipid in presence of $CaCl_2$ (M1 not according to the invention, M2 according to the invention)

| | Foam volume M1 > M2 | Foam volume M1 = M2 | Foam volume M1 < M2 |
|---|---|---|---|
| Result of the panel test, sum over all panelists | 2 | 5 | 3 |

TABLE S

Assessment of the toothpaste formulations containing SLS in absence of $CaCl_2$ (J1, J2 not according to the invention)

| | Foam volume J1 > J2 | Foam volume J1 = J2 | Foam volume J1 < J2 |
|---|---|---|---|
| Result of the panel test, sum over all panelists | 1 | 7 | 2 |

TABLE T

Assessment of the toothpaste formulations containing CAPB in absence of $CaCl_2$ (K1, K2 not according to the invention)

| | Foam volume K1 > K2 | Foam volume K1 = K2 | Foam volume K1 < K2 |
|---|---|---|---|
| Result of the panel test, sum over all panelists | 1 | 9 | 0 |

TABLE U

Assessment of the toothpaste formulations containing Rhamnolipid in absence of CaCl$_2$ (L1 not according to the invention, L2 according to the invention)

| | Foam volume L1 > L2 | Foam volume L1 = L2 | Foam volume L1 < L2 |
|---|---|---|---|
| Result of the panel test, sum over all panelists | 2 | 8 | 0 |

TABLE V

Assessment of the toothpaste formulations containing Sophorolipid in absence of CaCl$_2$ (M1 not according to the invention, M2 according to the invention)

| | Foam volume M1 > M2 | Foam volume M1 = M2 | Foam volume M1 < M2 |
|---|---|---|---|
| Result of the panel test, sum over all panelists | 1 | 8 | 1 |

The paired sensory comparison has shown that the presence of fluoride in a Rhamnolipid or Sophorolipid containing toothpaste formulation has no influence on the foam volume independent of the water hardness of the water which is used during the application, whereas the foam volume is reduced in the corresponding formulations containing fluoride and SLS or fluoride and CAPB. The reduction of foam is believed to be caused by the precipitation of Calcium-Flouride; the precipation has thus two negative impacts: i) the foam volume is reduced which has impact on the sensorial quality of the toothpaste during application ii) Flouride which is precipitated by calcium is not available for the remineralization and the formation of the fluorapatite mineral phase.

EXAMPLE FORMULATIONS

The following examples are for the purpose of illustration and are not to be construed as limitations of the present invention since many variations thereof are possible without departing from its scope.

The compositions are made using conventional methods. The pH value, if necessary, was adjusted by addition of either aqueous sodium hydroxide or citric acid.

Example Formulation 1 a,b: Toothpaste

| Ingredient | % w/w | % w/w |
|---|---|---|
| Aqua | q.s. to 100 | q.s. to 100 |
| Glycerin | 29.0 | 29.0 |
| Sodium Metaphosphate | 12.0 | 12.0 |
| Hydrated Silica (Hydrated) | 10.0 | 10.0 |
| Xylitol | 10.0 | 10.0 |
| Rhamnolipid | 1.0 | |
| Sophorolipid | | 1.0 |
| Olaflur | 0.13 | 0.13 |
| Cocamidopropyl Betaine | 0.5 | 0.5 |
| Propylene Glycol | 1.0 | 1.0 |
| *Chamomilla recutita* flower extract | 0.4 | 0.4 |
| Alcohol denat | 0.5 | 0.5 |
| Panthenol | 0.1 | 0.1 |
| Sodium fluoride | 0.1 | 0.1 |
| Hydroxyethylcellulose | 1.0 | 1.0 |
| Titanium dioxide | 0.4 | 0.4 |
| Aroma | 1.0 | 1.0 |
| Citronellol | 0.0 | 0.0 |
| Eucalyptol | 0.2 | 0.2 |
| Eugenol | 0.1 | 0.1 |
| Menthol | 0.15 | 0.15 |
| Color, pH adjuster, preservative | q.s. | q.s. |

Example Formulation 2 a,b: Toothpaste

| Ingredient | % w/w | % w/w |
|---|---|---|
| Aqua | q.s. to 100 | q.s. to 100 |
| Hydrated Silica (Hydrated) | 22.0 | 22.0 |
| Sorbitol | 30.0 | 30.0 |
| Hydroxyethylcellulose | 1.5 | 1.5 |
| Rhamnolipid | 1.0 | |
| Sophorolipid | | 1.0 |
| Olaflur | 0.19 | 0.19 |
| Aroma | 1.0 | 1.0 |
| Limonene | 0.1 | 0.1 |
| Titanium Dioxide | 0.3 | 0.3 |
| Saccharin | 0.2 | 0.2 |
| Color, pH adjuster, preservative | q.s. | q.s. |

Example Formulation 3 a,b: Toothpaste

| Ingredient | % w/w | % w/w |
|---|---|---|
| Sorbitol | 45.0 | 45.0 |
| Aqua | q.s. to 100 | q.s. to 100 |
| Hydrated Silica (Hydrated) | 18.0 | 18.0 |
| Sodium Lauryl Sulfate | 1.05 | 1.05 |
| Rhamnolipid | 0.75 | |
| Sophorolipid | | 0.75 |
| PEG-32 | 1.0 | 1.0 |
| Flavor | 1.0 | 1.0 |
| Cellulose Gum | 0.8 | 0.8 |
| Cocamidopropyl Betaine | 0.35 | 0.35 |
| Sodium Saccharin | 0.2 | 0.2 |
| Sodium Fluoride | 0.23 | 0.23 |
| Zinc Sulfate | 0.3 | 0.3 |
| Mica | 0.5 | 0.5 |
| Color solution (1% FD&C Blue No. 1) | 0.02 | 0.02 |
| Titanium Dioxide | 0.3 | 0.3 |
| Eugenol | 0.2 | 0.2 |
| pH adjuster, preservative | q.s. | q.s. |

Example Formulation 4: Toothpaste

| Ingredient | % w/w |
|---|---|
| Glycerin | 35.0 |
| Hydrated Silica (Hydrated) | 22.0 |
| Aqua | q.s. to 100 |
| Sodium Bicarbonate | 20.0 |
| PEG-12 | 3.0 |
| Rhamnolipid | 1.5 |
| Sodium Lauryl Sulfate | 1.0 |
| Flavor | 1.0 |
| Sodium Hydroxide | 0.9 |
| Cellulose Gum | 0.9 |
| *Chondrus Crispus* | 0.5 |

-continued

| Ingredient | % w/w |
| --- | --- |
| Sodium Saccharin | 0.1 |
| Calcium Peroxide | 0.1 |
| Titanium Dioxide | 0.4 |
| Sodium monofluorophosphate | 0.76 |
| PH adjuster, preservative | q.s. |

Example Formulation 5: Toothpaste

| Ingredient | % w/w |
| --- | --- |
| Aqua | q.s. to 100 |
| Glycerin | 33.0 |
| Hydrated Silica (Hydrated) | 24.0 |
| Rhamnolipid | 1.5 |
| Cellulose Gum | 0.8 |
| Aroma | 0.9 |
| Sodium Fluoride | 0.23 |
| Sodium Saccharin | 0.2 |
| *Commiphora Myrrha* Oil | 0.05 |
| *Salvia Officinalis* Oil | 0.05 |
| *Mentha Piperita* Oil | 0.2 |
| *Chamomilla Recutita* Flower Extract | 0.2 |
| Limonene | 0.1 |
| Titanium Dioxide | 0.3 |
| Color solution (1% FD&C Blue No. 1) | 0.05 |
| pH adjuster, preservative | q.s. |

Example Formulation 6: Toothpaste

| Ingredient | % w/w |
| --- | --- |
| Glycerin | 27.0 |
| Hydrated Silica (Hydrated) | 21.0 |
| Sodium Hexametaphosphate | 13.0 |
| Aqua | q.s. to 100 |
| PEG-6 | 5.0 |
| Flavor | 1.0 |
| Trisodium Phosphate | 1.0 |
| Sodium Lauryl Sulfate | 1.05 |
| Rhamnolipid | 0.35 |
| *Chondrus Crispus* | 0.7 |
| Cocamidopropyl Betaine | 0.1 |
| Sodium Saccharin | 0.2 |
| Polyethylene Glycol | 0.5 |
| Xanthan Gum | 0.7 |
| Sucralose | 0.5 |
| Mica | 0.3 |
| Titanium Dioxide | 0.5 |
| Sodium Fluoride | 0.32 |
| Color, pH adjuster, preservative | q.s. |

Example Formulation 7: Toothpaste

| Ingredient | % w/w |
| --- | --- |
| Aqua | q.s. to 100 |
| Sorbitol | 29.0 |
| Hydrated Silica (Hydrated) | 22.0 |
| Disodium Pyrophosphate | 5.0 |
| Rhamnolipid | 1.2 |
| Cellulose Gum | 1.2 |
| Aroma | 0.9 |
| Sodium Bicarbonate | 0.8 |

-continued

| Ingredient | % w/w |
| --- | --- |
| Carbomer | 0.8 |
| Sodium Fluoride | 0.32 |
| Sodium Saccharin | 0.1 |
| Xanthan Gum | 0.5 |
| Titanium Dioxide | 0.5 |
| Limonene | 0.2 |
| Color, pH adjuster, preservative | q.s. |

Example Formulation 8: Toothpaste

| Ingredient | % w/w |
| --- | --- |
| Aqua | q.s. to 100 |
| Hydrated Silica (Hydrated) | 21.0 |
| Sorbitol | 19.0 |
| Glycerin | 15.0 |
| Propylene Glycol | 5.0 |
| Tetrapotassium Pyrophosphate | 5.0 |
| Pentasodium Triphosphate | 5.0 |
| Sodium C14-16 Olefin Sulfonate | 1.0 |
| Rhamnolipid | 1.0 |
| Disodium Pyrophosphate | 0.7 |
| Aroma | 1.0 |
| Titanium Dioxide | 0.4 |
| Xanthan Gum | 0.7 |
| Sodium Fluoride | 0.32 |
| Sodium Saccharin | 0.15 |
| Allantoin | 0.2 |
| *Chamomilla Recutita* Flower Extract | 0.1 |
| *Salvia Officinalis* Leaf Extract | 0.2 |
| Zinc Chloride | 0.3 |
| Color solution (1% FD&C Blue No. 1) | 0.05 |
| pH adjuster, preservative | q.s. |

Example Formulation 9: Toothpaste

| Ingredient | % w/w |
| --- | --- |
| Aqua | q.s. to 100 |
| Hydrated Silica (Hydrated) | 21.0 |
| Xylitol | 10.0 |
| Sorbitol | 10.0 |
| Rhamnolipid | 1.5 |
| Betaine | 0.5 |
| *Aloe Barbadensis* Leaf Juice Powder | 0.3 |
| Xanthan Gum | 0.5 |
| Zinc Gluconate | 0.5 |
| Sodium Coco-sulfate | 0.5 |
| *Mentha Spicata Crispa* Herb Oil | 0.1 |
| *Calendula Officinalis* Flower Extract | 0.2 |
| *Chamomilla Recutita* Flower Extract | 0.2 |
| L-limonene | 0.1 |
| *Mentha Arvensis* Leaf Oil | 0.1 |
| Sodium Fluoride | 0.32 |
| Titanium Dioxide | 0.4 |
| PH adjuster, preservative | q.s. |

Example Formulation 10: Toothpaste

| Ingredient | % w/w |
| --- | --- |
| Aqua | q.s. to 100 |
| Hydroxyapatite | 20.0 |

-continued

| Ingredient | % w/w |
|---|---|
| Propylene Glycol | 10.0 |
| Glycerin | 10.0 |
| Sorbitol | 10.0 |
| Tetrapotassium Pyrophosphate | 7.0 |
| Silica | 7.0 |
| Rhamnolipid | 1.0 |
| Aroma | 1.0 |
| Cellulose Gum | 1.0 |
| Sodium C14-16 Olefin Sulfonate | 1.0 |
| Sodium Fluoride | 0.32 |
| Sodium Cocoyl Isethionate | 0.5 |
| Sodium Saccharin | 0.15 |
| Limonene | 0.2 |
| Titanium Dioxide | 0.4 |
| Color, pH adjuster, preservative | q.s. |

Example Formulation 11: Toothpaste

| Ingredient | % w/w |
|---|---|
| Aqua | q.s. to 100 |
| Hydrogenated Starch Hydrolysate (Hydrogenated, Hydrolysed) | 20.0 |
| Hydrated Silica (Hydrated), | 15.0 |
| Glycerin | 15.0 |
| Alumina | 10.0 |
| Sodium Lauryl Sulfate | 1.05 |
| PEG-12 | 1.0 |
| Rhamnolipid | 0.75 |
| Perlite | 0.5 |
| Pentapotassium Triphosphate | 0.8 |
| Pentasodium Triphosphate | 0.8 |
| Sodium Monofluorophosphate | 0.76 |
| Cellulose Gum | 0.9 |
| Sodium Saccharin | 0.2 |
| Cocamidopropyl Betaine | 0.35 |
| Aroma | 1.0 |
| Limonene | 0.1 |
| Color solution (1% FD&C Blue No. 1) | 0.05 |
| Titanium Dioxide | 0.3 |
| pH adjuster, preservative | q.s. |

Example Formulation 12: Toothpaste

| Ingredient | % w/w |
|---|---|
| Dicalcium Phosphate Dihydrate (Dihydrate) | 25.0 |
| Aqua | q.s. to 100 |
| Sorbitol | 20.0 |
| Glycerin | 20.0 |
| Methyl Salicylate | 1.0 |
| Sodium Lauryl Sulfate | 0.9 |
| Rhamnolipid | 0.9 |
| Titanium Dioxide | 0.5 |
| Chondrus Crispus | 0.8 |
| Cellulose Gum | 0.5 |
| Sodium Silicate | 0.3 |
| Hydrated Silica (Hydrated) | 1.0 |
| Thymol | 0.1 |
| Sodium Saccharin | 0.2 |
| Sodium Hydroxide | 0.5 |
| Menthol | 0.3 |
| Color solution (1% FD&C Blue No. 1) | 0.02 |
| pH adjuster, preservative | q.s. |

Example Formulation 13: Toothpaste

| Ingredient | % w/w |
|---|---|
| Aqua | q.s. to 100 |
| Hydrated Silica (Hydrated) | 21.0 |
| Sorbitol | 21.0 |
| Glycerin | 18.0 |
| PEG-6 | 5.0 |
| Rhamnolipid | 1.5 |
| Xanthan Gum | 0.8 |
| Flavor | 0.7 |
| Titanium Dioxide | 0.5 |
| Sodium Citrate | 0.4 |
| Sodium Fluoride | 0.32 |
| Zinc Chloride | 0.5 |
| Sodium Saccharin | 0.2 |
| Chondrus Crispus | 0.7 |
| Limonene | 0.1 |
| Color solution (1% FD&C Blue No. 1) | 0.04 |
| pH adjuster, preservative | q.s. |

Example Formulation 14: Toothpaste

| Ingredient | % w/w |
|---|---|
| Aqua | q.s. to 100 |
| Sorbitol | 36.0 |
| Hydrated Silica (Hydrated), | 18.0 |
| Glycerin | 18.0 |
| Potassium Nitrate | 1.0 |
| Aroma | 1.0 |
| Cocamidopropyl Betaine | 1.0 |
| Rhamnolipid | 1.0 |
| Xanthan Gum | 0.7 |
| Sodium Saccharin | 0.2 |
| Sodium Fluoride | 0.32 |
| Mica | 0.4 |
| Titanium Dioxide | 0.4 |
| Sodium Hydroxide | 0.5 |
| Limonene | 0.1 |
| Eugenol | 0.1 |
| Color, pH adjuster, preservative | q.s. |

Example Formulation 15: Toothpaste

| Ingredient | % w/w |
|---|---|
| Glycerin | 33.0 |
| PEG-8 | 5.0 |
| Hydrated Silica (Hydrated), | 5.0 |
| Calcium Sodium Phosphosilicate | 3.0 |
| Cocamidopropyl Betaine | 1.0 |
| Rhamnolipid | 1.0 |
| Sodium Methyl Cocoyl Taurate | 0.3 |
| Aroma | 0.8 |
| Titanium Dioxide | 0.5 |
| Carbomer | 0.5 |
| Sodium Saccharin | 0.2 |
| Sodium Fluoride | 0.32 |
| Limonene | 0.2 |
| Color, pH adjuster, preservative | q.s. |

Example Formulation 16: Toothpaste

| Ingredient | % w/w |
| --- | --- |
| Aqua | q.s. to 100 |
| Sorbitol | 63.0 |
| Hydrated Silica (Hydrated) | 14.0 |
| Silica | 7.0 |
| Titanium Dioxide | 0.6 |
| Maris Sal | 0.5 |
| Rhamnolipid | 0.9 |
| Sodium Cocoyl Glutamate | 0.5 |
| Disodium Cocoyl Glutamate | 0.5 |
| Xanthan Gum | 0.7 |
| Sodium Fluoride | 0.32 |
| *Echinacea Purpurea* Extract (Extract) | 0.1 |
| *Arnica Montana* Flower Extract | 0.1 |
| *Mentha Piperita* Leaf Water | 0.1 |
| *Myrtus Communis* Leaf Water | 0.1 |
| Glycerin | 1.0 |
| Menthol | 0.2 |
| Aroma | 1.0 |
| L-limonene | 0.2 |
| Color, pH adjuster, preservative | q.s. |

Example Formulation 17: Toothpaste

| Ingredient | % w/w |
| --- | --- |
| Sorbitol | 33.0 |
| Aqua | q.s. to 100 |
| Hydrated Silica (Hydrated) | 18.0 |
| Glycerin | 15.0 |
| PEG-32 | 4.0 |
| Sodium Lauryl Sulfate | 1.5 |
| Cellulose Gum | 1.0 |
| Rhamnolipid | 1.0 |
| Sodium Saccharin | 0.3 |
| Eucalyptol | 0.2 |
| Methyl Salicylate | 0.5 |
| Thymol | 0.1 |
| Phosphoric Acid | 0.3 |
| Menthol | 0.4 |
| Zinc Citrate | 0.5 |
| Sodium Phosphate | 0.2 |
| Xanthan Gum | 0.5 |
| Benzoic Acid | 0.2 |
| Sodium Monofluorophosphate | 0.76 |
| Flavor | 1.0 |
| Color solution (1% FD&C Blue No. 1) | 0.05 |
| pH adjuster, preservative | q.s. |

Example Formulation 18: Toothpaste

| Ingredient | % w/w |
| --- | --- |
| Hydrogenated Starch Hydrolysate (Hydrogenated, Hydrolysed) | 30.0 |
| Aqua | q.s. to 100 |
| Hydrated Silica (Hydrated) | 22.0 |
| PEG-32 | 4.0 |
| Rhamnolipid | 1.0 |
| Aroma | 1.0 |
| Cellulose Gum | 1.0 |
| Sodium Fluoride | 0.32 |
| Sodium Saccharin | 0.25 |
| PVM/MA Copolymer | 0.7 |
| Trisodium Phosphate | 0.8 |
| Calcium Aluminum Borosilicate | 0.4 |
| Glycerin | 0.9 |
| Lecithin | 0.2 |
| Tin Oxide | 0.2 |
| Limonene | 0.1 |
| Color solution (1% FD&C Blue No. 1) | 0.04 |
| Titanium Dioxide | 0.3 |
| pH adjuster, preservative | q.s. |

Example Formulation 19: Toothpaste

| Ingredient | % w/w |
| --- | --- |
| Aqua | q.s. to 100 |
| Sorbitol | 50.0 |
| Hydrated Silica (Hydrated), | 14.0 |
| Silica Dimethyl Silylate | 3.5 |
| Hydroxyethylcellulose | 3.5 |
| Rhamnolipid | 1.05 |
| PEG-40 Hydrogenated Castor Oil (Hydrogenated) | 0.8 |
| Aroma | 0.9 |
| Sodium Gluconate | 0.4 |
| Limonene | 0.1 |
| PEG-3 tallow aminopropyl amine | 0.5 |
| Olaflur | 0.06 |
| Stannous Fluoride | 0.4 |
| Sodium Saccharin | 0.2 |
| Potassium Hydroxide | 0.4 |
| Hydrochloric Acid | 0.2 |
| Color solution (1% FD&C Blue No. 1) | 0.04 |
| pH adjuster, preservative | q.s. |

Example Formulation 20: Toothpaste

| Ingredient | % w/w |
| --- | --- |
| Aqua | q.s. to 100 |
| Sorbitol | 45.0 |
| Hydrated Silica (Hydrated) | 21.0 |
| Sodium Lauryl Sulfate | 1.5 |
| Rhamnolipid | xx |
| Cellulose Gum | 1.0 |
| Aroma | 1.0 |
| Zinc Citrate | 0.5 |
| *Chondrus Crispus* Powder (Powdered) | 0.8 |
| Sodium Saccharin | 0.2 |
| Sodium Fluoride | 0.1 |
| Titanium Dioxide | 0.5 |
| Hydroxyethylcellulose | 0.3 |
| Sodium Citrate | 0.2 |
| Stannous Fluoride | 0.4 |
| Color, pH adjuster, preservative | q.s. |

Example Formulation 21: Toothpaste

| Ingredient | % w/w |
| --- | --- |
| Sodium Bicarbonate | 35.00 |
| PEG-8 | 5.0 |
| Hydrated Silica (Hydrated | 18.0 |
| Glycerin | 18.0 |
| Rhamnolipid | 1.0 |
| Sodium Lauryl Sulfate | 0.5 |
| Sodium Saccharin | 0.5 |
| Aroma | 0.9 |

| Ingredient | % w/w |
|---|---|
| Dipotassium Phosphate | 0.8 |
| Sodium Carbonate | 0.5 |
| Sodium Fluoride | 0.32 |
| PEG/PPG-116/66 Copolymer | 0.8 |
| Calcium Peroxide | 0.5 |
| Calcium Hydroxide | 0.4 |
| Color solution (1% FD&C Blue No. 1) | 0.04 |
| Sodium Silicate | 0.5 |
| Limonene | 0.1 |
| Silica | 0.9 |
| Titanium Dioxide | 0.3 |
| Color, pH adjuster, preservative | q.s. |

Example Formulation 22: Toothpaste

| Ingredient | % w/w |
|---|---|
| Glycerin | 33.0 |
| Hydrated Silica | 22.0 |
| Aqua | q.s. to 100 |
| Sorbitol | 15.0 |
| Tetrapotassium Pyrophosphate | 3.5 |
| Rhamnolipid | 1.5 |
| Titanium Dioxide | 0.4 |
| Sodium Lauroyl Sarcosinate | 0.5 |
| Cellulose Gum | 0.8 |
| Lauryl Glucoside | 0.5 |
| PVP | 0.5 |
| Cocamidopropyl Betaine | 0.5 |
| Xanthan Gum | 0.5 |
| Stannous Fluoride | 0.4 |
| Color, pH adjuster, preservative | q.s. |

Example Formulation 23: Toothpaste

| Ingredient | % w/w |
|---|---|
| Aqua | q.s. to 100 |
| Hydrated Silica (Hydrated) | 20.0 |
| Sorbitol | 18.0 |
| Xylitol | 14.0 |
| Rhamnolipid | 1.2 |
| Propylene Glycol | 1.0 |
| Glycerin | 1.0 |
| Sodium C14-16 Olefin Sulfonate | 0.3 |
| Aroma | 1.0 |
| Xanthan Gum | 0.5 |
| Disodium Phosphate | 0.4 |
| Sodium Fluoride | 0.32 |
| Zinc Chloride | 0.5 |
| Sodium Saccharin | 0.2 |
| Citric Acid | 0.2 |
| Titanium Dioxide | 0.4 |
| Color, pH adjuster, preservative | q.s. |

Example Formulation 24: Toothpaste

| Ingredient | % w/w |
|---|---|
| Aqua | q.s. to 100 |
| Hydrogenated Starch Hydrolysate (Hydrogenated, Hydrolysed) | 25.0 |
| Hydrated Silica (Hydrated) | 21.0 |
| Hydroxyapatite | 4.5 |
| PEG-32 | 4.5 |
| Rhamnolipid | 1.0 |
| Sodium Lauryl Sulfate | 0.5 |
| Aroma | 0.9 |
| Sodium Monofluorophosphate | 0.76 |
| Trisodium Phosphate | 0.5 |
| Cellulose Gum | 1.0 |
| Sodium Saccharin | 0.2 |
| Sodium Hydroxide | 0.3 |
| Limonene | 0.1 |
| Color solution (1% FD&C Blue No. 1) | 0.05 |
| Titanium Dioxide | 0.4 |
| pH adjuster, preservative | q.s. |

Example Formulation 25: Toothpaste

| Ingredient | % w/w |
|---|---|
| Glycerin | 32.0 |
| Hydrated Silica (Hydrated) | 21.0 |
| Aqua | q.s. to 100 |
| Sodium Bicarbonate | 30.0 |
| PEG-12 | 3.0 |
| Rhamnolipid | 1.5 |
| Sodium Lauryl Sulfate | 1.0 |
| Flavor | 1.0 |
| Sodium Hydroxide | 1.0 |
| Cellulose Gum | 1.0 |
| *Chondrus Crispus* | 0.7 |
| Sodium Saccharin | 0.15 |
| Calcium Peroxide | 0.5 |
| Titanium Dioxide | 0.5 |
| Sodium Monofluorophosphate | 0.76 |
| Color, pH adjuster, preservative | q.s. |

Example Formulation 26: Toothpaste

| Ingredient | % w/w |
|---|---|
| Aqua | q.s. to 100 |
| Sorbitol | 63.0 |
| Hydrated Silica (Hydrated) | 22.0 |
| Propylene Glycol | 1.5 |
| Cellulose Gum | 1.5 |
| Rhamnolipid | 1.0 |
| Sodium C 14-16 Olefin Sulfonate | 0.5 |
| Aroma | 0.8 |
| Calcium Glycerophosphate | 0.4 |
| Sodium Fluoride | 0.11 |
| Sodium Saccharin | 0.4 |
| Cocamidopropyl Betaine | 0.5 |
| Citral | 0.1 |
| Geraniol | 0.1 |
| Limonene | 0.1 |
| Linalool | 0.1 |
| Titanium Dioxide | 0.2 |
| Color, pH adjuster, preservative | q.s. |

Example Formulation 27: Toothpaste

| Ingredient | % w/w |
|---|---|
| Aqua | q.s. to 100 |
| Calcium Carbonate | 30.0 |
| Silica | 7.0 |
| Glycerin | 5.0 |
| Hydrated Silica | 2.5 |
| Rhamnolipid | 1.5 |
| Aroma | 1.0 |
| *Chondrus Crispus* Powder | 0.5 |
| Cellulose Gum | 0.5 |
| Chlorhexidine Gluconate | 0.1 |
| Limonene | 0.15 |
| Sodium Saccharin | 0.15 |
| Titanium Dioxide | 0.1 |
| Sodium Fluoride | 0.32 |
| Color, pH adjuster, preservative | q.s. |

Example Formulation 28: Toothpaste

| Ingredient | % w/w |
|---|---|
| Aqua | q.s. to 100 |
| Hydrogenated Starch Hydrolysate | 20.0 |
| Hydrated Silica | 15.0 |
| PEG-32 | 4.0 |
| Rhamnolipid | 1.0 |
| Propylene Glycol | 0.9 |
| Aroma | 0.9 |
| Sodium Lauryl Sulfat | 0.5 |
| Hydroxyethylcellulose | 0.5 |
| Olaflur | 0.13 |
| Titanium Dioxide | 0.1 |
| Sodium Fluoride | 0.1 |
| Sodium Saccharin | 0.2 |
| *Chamomilla Recutita* Flower Extract | 0.2 |
| Chlorhexidine Digluconate | 0.1 |
| Limonene | 0.1 |
| Citral | 0.1 |
| Color, pH adjuster, preservative | q.s. |

Example Formulation 29: Toothpaste

| Ingredient | % w/w |
|---|---|
| Aqua | q.s. to 100 |
| Sorbitol | 20.0 |
| Hydrated Silica | 15.0 |
| Silica | 2.0 |
| Rhamnolipid | 1.0 |
| Cocamidopropyl Betaine | 0.75 |
| Titanium Dioxide | 0.15 |
| Flavor | 0.8 |
| Linalool | 0.2 |
| Sodium Monofluorophosphate | 0.76 |
| Sodium Fluoride | 0.1 |
| Sodium Saccharin | 0.25 |
| Cellulose Gum | 0.5 |
| Limonene | 0.1 |
| Chlorhexidine Digluconate | 0.12 |
| Color, pH adjuster, preservative | q.s. |

Example Formulation 30: Toothpaste

| Ingredient | % w/w |
|---|---|
| Aqua | q.s. to 100 |
| Hydrated Silica | 15.0 |
| Glycerin | 15.0 |
| Potassium Nitrate | 5.0 |
| Sorbitol | 4.5 |
| Sodium Cocoamphoacetate | 0.5 |
| Rhamnolipid | 0.5 |
| PEG-40 Hydrogenated Castor Oil | 0.5 |
| Carboxymethyl Cellulose | 0.5 |
| Titanium Dioxide | 0.1 |
| Sodium Fluoride | 0.32 |
| Sodium Saccharin | 0.2 |
| Aroma | 0.2 |
| Chlorhexidine Digluconate | 0.12 |
| Color, pH adjuster, preservative | q.s. |

Example Formulation 31 a,b: Toothpaste for Kids

| Ingredient | % w/w | % w/w |
|---|---|---|
| Aqua | q.s. to 100 | q.s. to 100 |
| Sorbitol | 28.0 | 28.0 |
| Hydrated Silica (Hydrated) | 18.0 | 18.0 |
| Hydroxyethylcellulose | 1.5 | 1.5 |
| Titanium Dioxide | 0.5 | 0.5 |
| Cocamidopropyl Betaine | 0.5 | 0.5 |
| Rhamnolipid | 0.5 | |
| Sophorolipid | | 0.5 |
| Olaflur | 0.07 | 0.07 |
| Aroma | 0.8 | 0.8 |
| Limonene | 0.1 | 0.1 |
| Sodium Saccharin | 0.2 | 0.2 |
| Hydrochloric Acid | 0.7 | 0.7 |
| Color, pH adjuster, preservative | q.s. | q.s. |

Example Formulation 32: Toothpaste for Children

| Ingredient | % w/w |
|---|---|
| Sorbitol | 33.0 |
| Aqua | q.s. to 100 |
| Hydrated Silica (Hydrated) | 22.0 |
| Rhamnolipid | 1.0 |
| Sodium C14-16 Olefin Sulfonate | 1.0 |
| Aroma | 0.8 |
| Cellulose Gum | 0.8 |
| Calcium Glycerophosphate | 0.5 |
| Olaflur | 0.07 |
| Sodium Fluoride | 0.1 |
| Propylene Glycol | 0.5 |
| Sodium Saccharin | 0.2 |
| Cocamidopropyl Betaine | 0.35 |
| Mica | 0.5 |
| Citral | 0.1 |
| Limonene | 0.1 |
| Linalool | 0.1 |
| Titanium Dioxide | 0.4 |
| Color solution (1% FD&C Blue No. 1) | 0.05 |
| Olaflur | 0.07 |
| pH adjuster, preservative | q.s. |

Example Formulation 33: Baby Toothpaste

| Ingredient | % w/w |
| --- | --- |
| Aqua | q.s. to 100 |
| Hydrogenated Starch Hydrolysate (Hydrogenated, Hydrolysed) | 14.0 |
| Hydrated Silica (Hydrated) | 14.0 |
| PEG-32 | 3.5 |
| Silica | 7.0 |
| Rhamnolipid | 1.5 |
| Cellulose Gum | 1.0 |
| Aroma | 1.0 |
| Propylene Glycol | 0.7 |
| PEG-40 Hydrogenated Castor Oil (Hydrogenated), | 0.8 |
| Olaflur | 0.06 |
| Sodium Chloride | 0.2 |
| Sodium Saccharin | 0.15 |
| Tocopheryl Acetate | 0.1 |
| Glycerin | 1.0 |
| Retinyl Palmitate | 0.1 |
| Color solution (1% FD&C Blue No. 1) | 0.02 |
| pH adjuster, preservative | q.s. |

Example Formulation 34: Toothpaste for Children

| Ingredient | % w/w |
| --- | --- |
| Aqua | q.s. to 100 |
| Hydrated Silica (Hydrated) | 22.0 |
| Glycerin | 20.0 |
| Xylitol | 10.0 |
| Rhamnolipid | 1.5 |
| Propylene Glycol | 0.7 |
| Xanthan Gum | 0.5 |
| Titanium Dioxide | 0.5 |
| Flavor | 0.9 |
| Sodium Lauroyl Sarcosinate | 0.5 |
| Disodium EDTA | 0.3 |
| Sodium Monofluorophosphate | 0.76 |
| Sodium Chloride | 0.2 |
| Color, pH adjuster, preservative | q.s. |

Example Formulation 35: Kids Toothpaste

| Ingredient | % w/w |
| --- | --- |
| Aqua | q.s. to 100 |
| Sorbitol | 40.0 |
| Hydrated Silica (Hydrated) | 17.0 |
| Glycerin | 26.0 |
| Rhamnolipid | 1.5 |
| Xanthan Gum | 1.0 |
| Steareth-30 | 1.0 |
| *Chondrus Crispus* | 1.0 |
| Aroma | 1.0 |
| Disodium Phosphate | 0.5 |
| Sodium Benzoate | 0.2 |
| Amyloglucosidase | 0.1 |
| Citric Acid | 0.3 |
| Zinc Gluconate | 0.5 |
| Glucose Oxidase | 0.1 |
| Sodium Fluoride | 0.22 |
| Sodium Saccharin | 0.15 |
| Potassium Thiocyanate | 0.1 |
| Lactoperoxidase | 0.1 |
| Titanium Dioxide | 0.3 |
| Color, pH adjuster, preservative | q.s. |

Example Formulation 36 a,b: 2 in 1 Toothpaste+Mouthwash

| Ingredient | % w/w | % w/w |
| --- | --- | --- |
| Sorbitol | 38.0 | 38.0 |
| Aqua | q.s. to 100 | q.s. to 100 |
| Hydrated Silica (Hydrated) | 21.0 | 21.0 |
| Pentasodium Triphosphate | 5.0 | 5.0 |
| Sodium Lauryl Sulfate | 0.35 | 0.35 |
| Rhamnolipid | 1.05 | 1.05 |
| Sophorolipid | | 1.0 |
| PEG-32 | 1.0 | |
| Aroma | 1.0 | 1.0 |
| Alumina | 0.5 | 0.5 |
| Alcohols | 0.7 | 0.7 |
| Xanthan Gum | 0.8 | 0.8 |
| Sodium Fluoride | 0.23 | 0.23 |
| Sodium Saccharin | 0.2 | 0.2 |
| Disodium Phosphate | 0.5 | 0.5 |
| Cocamidopropyl Betaine | 0.35 | 0.35 |
| Zinc Sulfate | 0.5 | 0.5 |
| Trisodium Phosphate | 0.3 | 0.3 |
| Sodium Chloride | 0.4 | 0.4 |
| Sodium Sulfate | 0.2 | 0.2 |
| Limonene | 0.1 | 0.1 |
| Titanium Dioxide | 0.5 | 0.5 |
| Color, pH adjuster, preservative | q.s. | q.s. |

Example Formulation 37 a,b: 2 in 1 Toothpaste+Mouthwash

| Ingredient | % w/w | % w/w |
| --- | --- | --- |
| Sorbitol | 29.0 | 29.0 |
| Aqua | q.s. to 100 | q.s. to 100 |
| Hydrated Silica | 15.0 | 15.0 |
| PEG-32 | 3.0 | 3.0 |
| Sodium Lauryl Sulfate | 0.5 | 0.5 |
| Rhamnolipid | 0.5 | |
| Sophorolipid | | 0.5 |
| Aroma | 0.9 | 0.9 |
| Alcohols | 0.7 | 0.7 |
| Xanthan Gum | 0.5 | 0.5 |
| PEG-30 Glyceryl Stearate | 0.5 | 0.5 |
| Sodium Fluoride | 0.05 | 0.05 |
| Sodium Saccharin | 0.7 | 0.7 |
| Disodium Phosphate | 0.3 | 0.3 |
| Cocamidopropyl Betaine | 0.5 | 0.5 |
| Zinc Sulfate | 0.3 | 0.3 |
| Trisodium Phosphate | 0.5 | 0.5 |
| Sodium Chloride | 0.1 | 0.1 |
| Sodium Sulfate | 0.2 | 0.2 |
| Limonene | 0.02 | 0.02 |
| Color, pH adjuster, Preservative | q.s. | q.s. |

Example Formulation 38 a,b: Mouthrinse without Alcohol

| Ingredient | % w/w | % w/w |
| --- | --- | --- |
| Aqua | q.s. to 100 | q.s. to 100 |
| Glycerin | 11.0 | 11.0 |
| Propylene Glycol | 7.0 | 7.0 |
| Rhamnolipid | 1.0 | |
| Sophorolipid | | 1.0 |
| Poloxamer 407 | 0.75 | 0.75 |
| Aroma | 0.9 | 0.9 |
| Cetylpyridinium Chloride | 0.04 | 0.04 |

| Ingredient | % w/w | % w/w |
|---|---|---|
| Sodium Fluoride | 0.05 | 0.05 |
| Sodium Saccharin | 0.07 | 0.07 |
| Menthol | 0.1 | 0.1 |
| Color, pH adjuster, Preservative | q.s. | q.s. |

Example Formulation 39: Mouthrinse without Alcohol

| Ingredient | % w/w |
|---|---|
| Aqua | q.s. to 100 |
| Sorbitol | 15.0 |
| Glycerin | 7.5 |
| Rhamnolipid | 1.0 |
| Xylitol | 1.0 |
| Cellulose Gum | 0.5 |
| Zinc PCA | 0.5 |
| Zinc Hydroxyapatite | 0.05 |
| Aroma | 0.9 |
| Silica | 0.05 |
| *Ricinus Communis* Seed Oil | 0.1 |
| Ammonium Acryloyldimethyltaurate/VP Copolymer | 0.05 |
| *Mentha Arvensis* Leaf Oil | 0.01 |
| Sodium Myristoyl Sarcosinate | 0.2 |
| Sodium Methyl Cocoyl Taurate | 0.2 |
| Sodium Saccharin | 0.5 |
| Sodium Fluoride | 0.05 |
| Limonene | 0.1 |
| Color, pH adjuster, Preservative | q.s. |

Example Formulation 40: Mouthrinse without Alcohol

| Ingredient | % w/w |
|---|---|
| Aqua | q.s. to 100 |
| Sorbitol | 20.0 |
| PEG-40 | 0.5 |
| Rhamnolipid | 0.5 |
| Flavor | 0.05 |
| Xanthan Gum | 0.1 |
| Zinc Sulfate | 0.15 |
| Sodium Saccharin | 0.05 |
| Sodium Fluoride | 0.05 |
| Gellan Gum | 0.2 |
| Calcium Aluminum Borosilicate | 0.1 |
| Silica | 0.05 |
| Titanium Dioxide | 0.05 |
| Tin Oxide | 0.07 |
| Eugenol | 0.15 |
| Limonene | 0.05 |
| Linalool | 0.05 |
| Color, pH adjuster, Preservative | q.s. |

Example Formulation 41 a,b: Mouthrinse without Alcohol

| Ingredient | % w/w |
|---|---|
| Aqua | q.s. to 100 |
| Glycerin | 7.5 |
| Rhamnolipid | 0.2 |
| Flavor | 0.3 |
| Cetylpyridinium Chloride | 0.04 |
| Sodium Saccharin | 0.05 |
| Sucralose | 0.05 |
| Sodium Fluoride | 0.02 |
| Disodium Phosphate | 0.25 |
| Color, pH adjuster, Preservative | q.s. |

Example Formulation 42: Mouthrinse

| Ingredient | % w/w |
|---|---|
| Aqua | q.s. to 100 |
| Glycerin | 10.0 |
| Sorbitol | 10.0 |
| Cocamidopropyl Betaine | 1.0 |
| Rhamnolipid | 0.5 |
| Potassium Chloride | 0.1 |
| Propylene Glycol | 0.5 |
| Aroma | 0.25 |
| Sodium Fluoride | 0.02 |
| Olaflur | 0.16 |
| Potassium Acesulfame | 0.1 |
| Sodium Chloride | 0.1 |
| Limonene | 0.03 |
| Sodium Sulfate | 0.05 |
| Color, pH adjuster, Preservative | q.s. |

Example Formulation 43 a,b: Mouthrinse without Alcohol

| Ingredient | % w/w | % w/w |
|---|---|---|
| Aqua | q.s. to 100 | q.s. to 100 |
| Sorbitol | 15.0 | 15.0 |
| Rhamnolipid | 1.0 | |
| Sophorolipid | | 1.0 |
| *Aloe Barbadensis* Leaf Extract | 0.15 | 0.15 |
| *Calendula Officinalis* Flower Extract | 0.2 | 0.2 |
| *Chamomilla Recutita* Flower Extract | 0.2 | 0.2 |
| Sodium Fluoride | 0.02 | 0.02 |
| Calcium Glycerophosphate | 0.05 | 0.05 |
| Zinc Gluconate | 0.8 | 0.8 |
| *Mentha Spicata Crispa* Herb Oil | 0.05 | 0.05 |
| *Mentha Arvensis* Leaf Oil | 0.05 | 0.05 |
| Menthol | 0.04 | 0.04 |
| Color, pH adjuster, Preservative | q.s | q.s. |

Example Formulation 44 a,b: Mouthrinse without Alcohol

| Ingredient | % w/w | % w/w |
|---|---|---|
| Aqua | q.s. to 100 | q.s. to 100 |
| Glycerin | 15.0 | 15.0 |
| Sodium Gluconate | 1.5 | 1.5 |
| Rhamnolipid | 0.5 | |
| Sophorolipid | | 0.5 |
| PEG-40 Hydrogenated Castor Oil | 0.5 | 0.5 |
| Olaflur | 0.16 | 0.16 |
| Aroma | 0.25 | 0.25 |
| Stannous Chloride | 0.05 | 0.05 |
| Sodium Fluoride | 0.02 | 0.02 |

| Ingredient | % w/w | % w/w |
| --- | --- | --- |
| Cocamidopropyl Betaine | 0.35 | 0.35 |
| Sodium Saccharin | 0.07 | 0.07 |
| Color, pH adjuster, Preservative | q.s. | q.s. |

Example Formulation 45: Mouthrinse without Alcohol

| Ingredient | % w/w |
| --- | --- |
| Aqua | q.s. to 100 |
| Glycerin | 10.0 |
| Sorbitol | 8.0 |
| Rhamnolipid | 1.0 |
| Tetrasodium Pyrophosphate | 0.25 |
| Aroma | 0.04 |
| Limonene | 0.1 |
| Sodium Fluoride | 0.02 |
| Sodium Saccharin | 0.08 |
| Color, pH adjuster, Preservative | q.s. |

Example Formulation 46: Mouthrinse without Alcohol

| Ingredient | % w/w |
| --- | --- |
| Aqua | q.s. to 100 |
| Glycerin | 7.5 |
| PEG-60 Hydrogenated Castor Oil | 1.0 |
| Rhamnolipid | 0.5 |
| Sodium Citrate | 0.45 |
| Aroma | 0.3 |
| Zinc Chloride | 0.15 |
| Cetylpyridinium Chloride | 0.05 |
| Sodium Saccharin | 0.08 |
| Sodium Fluoride | 0.02 |
| Color, pH adjuster, Preservative | q.s. |

Example Formulation 47: Mouthrinse without Alcohol

| Ingredient | % w/w |
| --- | --- |
| Aqua | q.s. to 100 |
| Glycerin | 11.0 |
| Rhamnolipid | 2.0 |
| Flavor | 1.0 |
| Cetylpyridinium Chloride | 0.5 |
| Poloxamer 407 | 0.1 |
| Sodium Saccharin | 0.1 |
| Sodium Fluoride | 0.02 |
| Sucralose | 0.05 |
| Mentha Viridis Leaf Oil | 0.1 |
| Color, pH adjuster, Preservative | q.s. |

Example Formulation 48: Mouthrinse without Alcohol

| Ingredient | % w/w |
| --- | --- |
| Aqua | q.s. to 100 |
| Glycerin | 12.0 |
| Sorbitol | 8.0 |
| Potassium Nitrate | 0.15 |
| PEG-60 Hydrogenated Castor Oil | 0.5 |
| Rhamnolipid | 0.25 |
| Poloxamer 407 | 0.25 |
| Aroma | 0.2 |
| Disodium Phosphate, Sodium Phosphate | 0.25 |
| Sodium Fluoride | 0.05 |
| Sodium Saccharin | 0.08 |
| Color, pH adjuster, Preservative | q.s. |

Example Formulation 49: Mouthrinse without Alcohol

| Ingredient | % w/w |
| --- | --- |
| Aqua | q.s. to 100 |
| Sorbitol | 10.0 |
| PEG-40 Hydrogenated Castor Oil | 1.0 |
| Potassium Citrate | 1.0 |
| Rhamnolipid | 0.25 |
| Glycerin | 0.9 |
| Aroma | 0.4 |
| Zinc Sulfate | 0.15 |
| Sodium Saccharin | 0.1 |
| Propylene Glycol | 0.3 |
| *Citrus* Limon Juice | 0.05 |
| *Aloe Barbadensis* Leaf Extract | 0.1 |
| Limonene | 0.05 |
| Sodium Fluoride | 0.02 |
| Color, pH adjuster, Preservative | q.s. |

Example Formulation 50 Mouthrinse without Alcohol

| Ingredient | % w/w |
| --- | --- |
| Aqua | q.s. to 100 |
| Glycerin | 12.0 |
| Rhamnolipid | 1.2 |
| Hydrogenated Starch Hydrolysate | 1.0 |
| Xylitol | 1.0 |
| Steareth-30 | 0.2 |
| Amyloglucosidase | 0.5 |
| Allantoin | 0.1 |
| Glucose Oxidase | 0.5 |
| Sodium Fluoride | 0.05 |
| Limonene | 0.1 |
| Color, pH adjuster, Preservative | q.s. |

Example Formulation 51 a,b: Mouthrinse

| Ingredient | % w/w | % w/w |
| --- | --- | --- |
| Aqua | q.s. to 100 | q.s. to 100 |
| Glycerin | 11.0 | 11.0 |
| Propylene Glycol | 7.5 | 7.5 |

-continued

| Ingredient | % w/w | % w/w |
|---|---|---|
| Sorbitol | 7.5 | 7.5 |
| Tetrapotassium Pyrophosphate | 1.5 | 1.5 |
| Polysorbate 20 | 0.5 | 0.5 |
| Rhamnolipid | 0.5 | |
| Sophorolipid | | 0.5 |
| Tetrasodium Pyrophosphate | 0.75 | 0.75 |
| Zinc Citrate | 0.15 | 0.15 |
| PVM/MA Copolymer | 0.1 | 0.1 |
| Flavor | 0.2 | 0.2 |
| Sodium Fluoride | 0.05 | 0.05 |
| Sodium Saccharin | 0.07 | 0.07 |
| Color, pH adjuster, Preservative | q.s. | q.s. |

Example Formulation 52 a,b: Mouthrinse

| Ingredient | % w/w | % w/w |
|---|---|---|
| Aqua | q.s. to 100 | q.s. to 100 |
| Glycerin | 11.0 | 11.0 |
| Alcohol | 7.5 | 7.5 |
| Sorbitol | 7.5 | 7.5 |
| Rhamnolipid | | 1.0 |
| Sophorolipd | 1.0 | |
| Poloxamer 407 | 0.5 | 0.5 |
| Sodium Phosphate, Disodium Phosphate | 0.15 | 0.15 |
| Flavor | 0.9 | 0.9 |
| Cetylpyridinium Chloride | 0.05 | 0.05 |
| Sodium Saccharin | 0.08 | 0.08 |
| Sodium Fluoride | 0.05 | 0.05 |
| Color, pH adjuster, Preservative | q.s. | q.s. |

Example Formulation 53 a,b: Mouthrinse

| Ingredient | % w/w | % w/w |
|---|---|---|
| Aqua | q.s. to 100 | q.s. to 100 |
| Alcohols | 22.0 | 22.0 |
| Sorbitol | 10.0 | 10.0 |
| Flavor | 1.0 | 1.0 |
| Rhamnolipid | 1.0 | |
| Sophorolipid | | 1.0 |
| Sodium Saccharin | 0.09 | 0.09 |
| Eucalyptol | 0.1 | 0.1 |
| Thymol | 0.06 | 0.06 |
| Sucralose | 0.06 | 0.06 |
| Sodium Fluoride | 0.05 | 0.05 |
| Menthol | 0.04 | 0.04 |
| Color, pH adjuster, Preservative | q.s. | q.s. |

Example Formulation 54 a,b: Mouthrinse

| Ingredient | % w/w | % w/w |
|---|---|---|
| Aqua | q.s. to 100 | q.s. to 100 |
| Glycerin | 12.0 | 12.0 |
| Xylitol | 7.0 | 7.0 |
| Disodium Phosphate | 1.5 | 1.5 |
| Rhamnolipid | 1.0 | |
| Sophorolipid | | 1.0 |
| Cocamidopropyl Betaine | 0.5 | 0.5 |
| Propylene Glycol | 0.5 | 0.5 |
| Stannous Fluoride | 0.09 | 0.09 |
| Aroma | 0.3 | 0.3 |

-continued

| Ingredient | % w/w | % w/w |
|---|---|---|
| *Mentha Piperita* Leaf Extract | 0.1 | 0.1 |
| *Chamomilla Recutita* Flower Extract | 0.2 | 0.2 |
| *Salvia Officinalis* Leaf Extract | 0.25 | 0.25 |
| *Commiphora Myrrha* Resin Extract | 0.15 | 0.15 |
| Sodium Saccharin | 0.1 | 0.1 |
| Citral | 0.05 | 0.05 |
| Limonene | 0.02 | 0.02 |
| Linalool | 0.02 | 0.02 |
| Color, pH adjuster, Preservative | q.s. | q.s. |

Example Formulation 55 a,b: Mouthrinse

| Ingredient | % w/w | % w/w |
|---|---|---|
| Aqua | q.s. to 100 | q.s. to 100 |
| Glycerin | 11.0 | 11.0 |
| Sorbitol | 11.0 | 11.0 |
| Propylene Glycol | 3.0 | 3.0 |
| Disodium Pyrophosphate | 1.5 | 1.5 |
| PEG-40 Hydrogenated Castor Oil | 1.0 | 1.0 |
| Rhamnolipid | 0.5 | |
| Sophorolipid | | 0.5 |
| PVM/MA Copolymer | 0.5 | 0.5 |
| Tetrapotassium Pyrophosphate | 0.25 | 0.25 |
| Sodium Levulinate | 0.25 | 0.25 |
| Sodium Anisate | 0.25 | 0.25 |
| Olaflur | 0.16 | 0.16 |
| Aroma | 0.8 | 0.8 |
| Arginine | 0.8 | 0.8 |
| Sodium Saccharin | 0.07 | 0.07 |
| Sodium Fluoride | 0.02 | 0.02 |
| Color, pH adjuster, Preservative | q.s. | q.s. |

Example Formulation 56 a,b: Mouthrinse

| Ingredient | % w/w | % w/w |
|---|---|---|
| Aqua | q.s. to 100 | q.s. to 100 |
| Alcohol Denat. | 33.0 | 33.0 |
| Glycerin | 10.0 | 10.0 |
| Sorbitol | 8.0 | 8.0 |
| PEG-40 Hydrogenated Castor Oil | 1.0 | 1.0 |
| Rhamnolipid | 1.0 | |
| Sophorolipid | | 1.0 |
| Aroma | 0.6 | 0.6 |
| Menthol | 0.05 | 0.05 |
| Sodium Saccharin | 0.07 | 0.07 |
| Aluminum Lactate | 0.2 | 0.2 |
| Thymol | 0.06 | 0.06 |
| *Curcuma Xanthorrhiza* Root Extract | 0.05 | 0.05 |
| Sodium Fluoride | 0.02 | 0.02 |
| Color, pH adjuster, Preservative | q.s. | q.s. |

Example Formulation 57 a,b: Mouthrinse

| Ingredient | % w/w | % w/w |
|---|---|---|
| Aqua | q.s. to 100 | q.s. to 100 |
| Sorbitol | 12.5 | 12.5 |
| Propylene Glycol | 3.5 | 3.5 |
| Rhamnolipid | 0.5 | 0.5 |
| Sophorolipid | | 0.5 |
| Sodium Lauryl Sulfate | 0.5 | 0.5 |

-continued

| Ingredient | % w/w | % w/w |
|---|---|---|
| Poloxamer 407 | 0.5 | 0.5 |
| Flavor | 0.3 | 0.3 |
| Eucalyptol | 0.08 | 0.08 |
| Methyl Salicylate | 0.1 | 0.1 |
| Thymol | 0.05 | 0.05 |
| Stannous Fluoride | 0.09 | 0.09 |
| Menthol | 0.1 | 0.1 |
| Sodium Saccharin | 0.06 | 0.06 |
| Sucralose | 0.7 | 0.7 |
| *Camellia Sinensis* Leaf Extract | 0.05 | 0.05 |
| Color, pH adjuster, Preservative | q.s. | q.s. |

Example Formulation 58: Mouthrinse

| Ingredient | % w/w |
|---|---|
| Aqua | q.s. to 100 |
| Rhamnolipid | 1.0 |
| Eucalyptol | 0.9 |
| Zinc Chloride | 0.25 |
| Methyl Salicylate | 0.05 |
| Thymol | 0.05 |
| Levomenthol | 0.07 |
| Stannous Fluoride | 0.09 |
| Color, pH adjuster, Preservative | q.s. |

Example Formulation 59: Mouthrinse

| Ingredient | % w/w |
|---|---|
| Aqua | q.s. to 100 |
| Alcohol Denat. | 15.0 |
| Sorbitol | 5.0 |
| Glycine | 1.0 |
| Rhamnolipid | 1.0 |
| Aroma | 0.2 |
| Zinc Sulfate | 0.2 |
| Sodium Fluoride | 0.02 |
| Sodium Saccharin | 0.07 |
| Color, pH adjuster, Preservative | q.s. |

Example Formulation 60: Mouthrinse

| Ingredient | % w/w |
|---|---|
| Aqua | q.s. to 100 |
| Sorbitol | 11.0 |
| Alcohol Denat. | 11.0 |
| Xylitol | 5.0 |
| PEG-40 Hydrogenated Castor Oil | 0.75 |
| Rhamnolipid | 0.5 |
| Isopropyl Alcohol | 0.5 |
| Menthol | 0.05 |
| Sodium Citrate | 0.15 |
| *Mentha Piperita* Herb Oil | 0.25 |
| Sodium Saccharin | 0.08 |
| Methyl Diisopropyl Propionamide | 0.05 |
| Thymol | 0.07 |
| Sodium Fluoride | 0.05 |
| O-cymen-5-ol | 0.05 |
| Cyclodextrin | 0.07 |
| *Eugenia Caryophyllus* Leaf Oil | 0.1 |
| Propylene Glycol | 0.25 |

-continued

| Ingredient | % w/w |
|---|---|
| Butylene Glycol | 0.25 |
| *Psidium Guajava* Leaf Extract | 0.08 |
| *Phyllanthus Emblica* Fruit Extract | 0.08 |
| *Echinacea Purpurea* Root Extract | 0.08 |
| *Salvia Officinalis* Leaf Extract | 0.2 |
| Color, pH adjuster, Preservative | q.s. |

Example Formulation 61: Mouthrinse

| Ingredient | % w/w |
|---|---|
| Aqua | q.s. to 100 |
| Alcohols | 15.0 |
| Sorbitol | 7.0 |
| Sodium Lauroyl Sarcosinate | 1.0 |
| Rhamnolipid | 0.25 |
| PEG-40 Hydrogenated Castor Oil | 0.25 |
| Aroma | 0.4 |
| Cetylpyridinium Chloride | 0.04 |
| Sodium Citrate | 0.15 |
| Sodium Saccharin | 0.08 |
| Sodium Fluoride | 0.05 |
| Limonene | 0.05 |
| Color, pH adjuster, Preservative | q.s. |

Example Formulation 62: Mouthrinse

| Ingredient | % w/w |
|---|---|
| Aqua | q.s. to 100 |
| Alcohol denat. | 18.0 |
| Sorbitol | 8.0 |
| Aroma | 1.0 |
| Poloxamer 407 | 0.9 |
| Methyl salicylate | 0.2 |
| Sodium Saccharin | 0.2 |
| Sodium Fluoride | 0.05 |
| Rhamnolipid | 0.9 |
| Chlorhexidine Digluconate | 0.2 |
| PEG-40 Hydrogenated Castor Oil | 0.2 |
| Color, pH adjuster, Preservative | q.s. |

Example Formulation 63: Mouthrinse

| Ingredient | % w/w |
|---|---|
| Aqua | q.s. to 100 |
| Glycerin | 10.0 |
| Hydrogenated Starch Hydrolysate | 1.0 |
| PVP | 0.5 |
| Rhamnolipid | 0.5 |
| Aroma | 0.4 |
| Zinc Acetate | 0.2 |
| Sodium Fluoride | 0.32 |
| Potassium Acesulfame | 0.15 |
| Chlorhexidine Digluconate | 0.2 |
| Color, pH adjuster, Preservative | q.s. |

Example Formulation 64 a,b: Mouthrinse

| Ingredient | % w/w | % w/w |
|---|---|---|
| Aqua | q.s. to 100 | q.s. to 100 |
| Glycerin | 12.0 | 12.0 |
| Sorbitol | 7.0 | 7.0 |
| Rhamnolipid | 0.75 | |
| Sophorolipid | | 0.75 |
| PEG-40 Hydrogenated Castor Oil | 0.5 | 0.5 |
| Chlorhexidine Gluconate | 0.2 | 0.2 |
| Mentha Piperita Oil | 0.2 | 0.2 |
| Sodium Fluoride | 0.05 | 0.05 |
| Sodium Saccharin | 0.2 | 0.2 |
| Color, pH adjuster, Preservative | q.s. | q.s. |

Example Formulation 65 a,b: Mouthrinse

| Ingredient | % w/w | % w/w |
|---|---|---|
| Aqua | q.s. to 100 | q.s. to 100 |
| Glycerin | 15.0 | 15.0 |
| Macrogolglycerol Hydroxystearate | 7.0 | 7.0 |
| Sorbitol | 7.0 | 7.0 |
| Rhamnolipid | 0.5 | |
| Sophorolipid | | 0.5 |
| Cocamidopropyl Betaine | 0.2 | 0.2 |
| Sodium Fluoride | 0.02 | 0.02 |
| Chlorhexidine Digluconate | 0.2 | 0.2 |
| Flavor | 0.5 | 0.5 |
| Color, pH adjuster, Preservative | q.s. | q.s. |

Example Formulation 66 a,b: Mouthrinse Concentrate

| Ingredient | % w/w | % w/w |
|---|---|---|
| Propylene Glycol | 55.0 | 55.0 |
| Aqua | q.s. to 100 | q.s. to 100 |
| Aroma | 2.0 | 2.0 |
| Sodium Saccharin | 0.4 | 0.4 |
| Rhamnolipid | 0.75 | |
| Sophorolipid | | 0.75 |
| Polysorbate 20 | 0.25 | 0.25 |
| Commiphora Myrrha Oil | 2.0 | 2.0 |
| Salvia Officinalis Oil | 0.2 | 0.2 |
| Mentha Piperita Oil | 0.2 | 0.2 |
| Chamomilla Recutita Flower Extract | 0.2 | 0.2 |
| Limonene | 0.1 | 0.1 |
| Sodium Fluoride | 0.02 | 0.02 |
| Color, pH adjuster, Preservative | q.s. | q.s. |

Example Formulation 67 a,b: Mouthrinse Concentrate

| Ingredient | % w/w | % w/w |
|---|---|---|
| Propylene Glycol | 45.0 | 45.0 |
| PEG-6 | 5.0 | 5.0 |
| Aqua | q.s. to 100 | q.s. to 100 |
| Rhamnolipid | 1.0 | |
| Sophorolipid | | 1.0 |
| Bisabolol | 0.2 | 0.2 |
| Zinc Chloride | 0.25 | 0.25 |

-continued

| Ingredient | % w/w | % w/w |
|---|---|---|
| Cetylpyridinium Chloride | 0.1 | 0.1 |
| Sodium Saccharin | 0.5 | 0.5 |
| Sodium Fluoride | 0.05 | 0.05 |
| Salvia Officinalis Oil | 2.5 | 2.5 |
| Eugenol | 0.2 | 0.2 |
| Limonene | 0.1 | 0.1 |
| Linalool | 0.1 | 0.1 |
| Citronellol | 0.1 | 0.1 |
| Color, pH adjuster, Preservative | q.s. | q.s. |

Example Formulation 68 a,b: Mouthrinse Concentrate

| Ingredient | % w/w | % w/w |
|---|---|---|
| Alcohols | 55.0 | 55.0 |
| Aqua | q.s. to 100 | q.s. to 100 |
| Aroma | 1.5 | 1.5 |
| Rhamnolipid | 0.7 | |
| Sophorolipid | | 0.7 |
| Sodium C14-17 Alkyl Sulfonate | 0.7 | 0.7 |
| Mentha Arvensis Leaf Oil | 2.0 | 2.0 |
| Sodium Saccharin | 0.5 | 0.5 |
| Chamomilla Recutita Flower Extract | 0.5 | 0.5 |
| Commiphora Myrrha Resin Extract | 0.2 | 0.2 |
| Salvia Officinalis Leaf Extract | 0.2 | 0.2 |
| Sodium Fluoride | 0.02 | 0.02 |
| Limonene | 0.1 | 0.1 |
| Color, pH adjuster, Preservative | q.s. | q.s. |

Example Formulation 69 a,b: Peroxide Mouthrinse

| Ingredient | % w/w | % w/w |
|---|---|---|
| Aqua | q.s. to 100 | q.s. to 100 |
| Glycerin | 11.0 | 11.0 |
| Alcohol | 5.0 | 5.0 |
| $H_2O_2$ 35% | 4.30 | 4.30 |
| Polyphosphate | 1.0 | 1.0 |
| Menthol | 0.05 | 0.05 |
| Coolant | 0.02 | 0.02 |
| Flavor | 0.15 | 0.15 |
| Calcium Chloride | 0.03 | 0.03 |
| Rhamnolipid | 0.50 | |
| Sophorolipid | | 0.50 |
| Sodium Saccharin | 0.1 | 0.1 |
| Sodium Fluoride | 0.22 | 0.22 |
| Color, pH adjuster, Preservative | q.s. | q.s. |

Example Formulation 70 a,b: Fluoride Gel

| Ingredient | % w/w | % w/w |
|---|---|---|
| Aqua | q.s. to 100 | q.s. to 100 |
| Propylene Glycol | 30.0 | 30.0 |
| Hydroxyethylcellulose | 3.0 | 3.0 |
| Saccharin | 1.0 | 1.0 |
| Rhamnolipid | 0.5 | |
| Sophorolipid | | 0.5 |
| Pyrus Malus Fruit | 0.2 | 0.2 |
| Mentha Piperita Oil | 0.2 | 0.2 |
| Flavor | 0.5 | 0.5 |
| Aminofluoride Dectafluor | 0.29 | 0.29 |

-continued

| Ingredient | % w/w | % w/w |
| --- | --- | --- |
| Olaflur | 3.03 | 3.03 |
| Sodium Fluoride | 2.21 | 2.21 |
| Color, pH adjuster, Preservative | q.s. | q.s. |

Example Formulation 71 a,b: Fluoride Gel

| Ingredient | % w/w | % w/w |
| --- | --- | --- |
| Aqua | q.s. to 100 | q.s. to 100 |
| Sorbitol | 15.00 | 15.00 |
| Silica | 5.0 | 5.0 |
| PEG 600 | 3.5 | 3.5 |
| Tetrapotassium Pyrophosphate | 1.5 | 1.5 |
| Xanthan Gum | 0.5 | 0.5 |
| Sodium Lauryl Sulfate | 0.75 | 0.75 |
| Rhamnolipid | 0.75 | |
| Sophorolipid | | 0.75 |
| Aroma | 0.9 | 0.9 |
| Methol | 0.05 | 0.05 |
| Anethol | 0.05 | 0.05 |
| Citronellol | 0.2 | 0.2 |
| Sodium Fluoride | 5.0 | 5.0 |
| Color, pH adjuster, Preservative | q.s. | q.s. |

Example Formulation 72 a,b: Dental Floss

| Ingredient | % w/w | % w/w |
| --- | --- | --- |
| PTFE | q.s. to 100 | q.s. to 100 |
| Aroma | 1.0 | 1.0 |
| Acacia Senegal Gum | 0.7 | 0.7 |
| Cera Alba | 0.7 | 0.7 |
| Potassium Acesulfame | 0.5 | 0.5 |
| Sodium Lauryl Sulfate | 0.25 | 0.25 |
| Rhamnolipid | 0.25 | |
| Sophorolipid | | 0.25 |
| Glycerin | 0.7 | 0.7 |
| Silica | 0.5 | 0.5 |
| Sodium Fluoride | 0.22 | 0.22 |

Example Formulation 73 a,b: Teeth Wipe

| Ingredient | % w/w | % w/w |
| --- | --- | --- |
| Aqua | q.s. 100 | q.s. 100 |
| Alcohol Denat. | 30.00 | 30.00 |
| Glycerin | 20.00 | 20.00 |
| Stevia | 1.0 | 1.0 |
| Polysorbate 20 | 0.5 | 0.5 |
| Rhamnolipid | 0.5 | |
| Sophorolipid | | 0.5 |
| Preservative | q.s. | q.s. |
| Aroma | 1.0 | 1.0 |

Example Formulation 74 a,b: Chewing Gum

| Ingredient | % w/w | % w/w |
| --- | --- | --- |
| Gum base | q.s. to 100 | q.s. to 100 |
| Sorbit | 40.0 | 40.0 |
| Isomalt | 9.0 | 9.0 |
| Xylitol | 2.5 | 2.5 |
| Mannit D | 2.5 | 2.5 |
| Aspartame | 0.1 | 0.1 |
| Acesulfam K | 0.05 | 0.05 |
| Emulgum | 0.2 | 0.2 |
| Sorbitol | 12.00 | 12.00 |
| Glycerin | 1.0 | 1.0 |
| Rhamnolipid | 1.0 | |
| Sophorolipid | | 1.0 |
| Flavor | 1.0 | 1.0 |
| Sodium Fluoride | 0.05 | 0.05 |

The invention claimed is:

1. An oral care composition comprising from 0.005 wt. % to 20 wt. % of a biosurfactant and a fluoride ion source based on the total weight of the composition, wherein the fluoride ion source is contained in an amount sufficient to supply from 500 to 1500 ppm fluoride ion, based on the total weight of the composition, wherein the biosurfactant is a rhamnolipid and is contained in an amount from 0.1 wt. % to 2 wt. %, based on the total weight of the composition, wherein the rhamnolipid is a compound of formula (1)

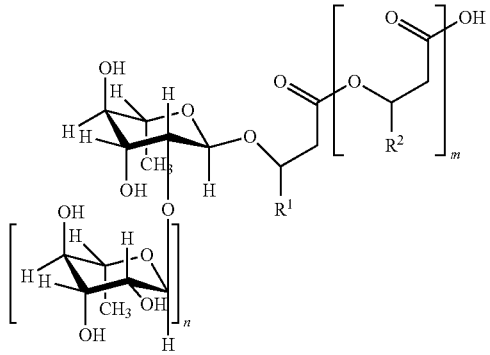

Formula (I)

wherein m is 1, n is 0 or 1

$R^1$ and $R^2$ are an organic radical having from 5 to 13 carbon atoms, wherein the rhamnolipid comprises from 51% by weight to 75% by weight of diRL-C10C10 and from 0.5% by weight to 2% by weight of monoRL-C10C10, wherein the weight ratio of the di-rhamnolipids and monorhamnolipids is greater than 90:10, and wherein the percentages by weight refer to the sum total of all rhamnolipids present.

2. The oral care composition according to claim 1, wherein the rhamnolipids comprise from 0.1% by weight to 25% by weight of diRL-C8C10, wherein the percentages by weight refer to the sum total of all biosurfactant present.

3. The oral care composition according to claim 1, wherein the fluoride ion source is selected from the group consisting of stannous fluoride, sodium fluoride, potassium fluoride, potassium monofluorophosphate, sodium monofluorophosphate, ammonium monofluorophosphate, sodium fluorosilicate, ammonium fluorosilicate, amine fluorides such as olaflur N'-octadecyltrimethylendiamine-N,N,N'-tris (2-ethanol)-dihydrofluoride and ammonium fluoride.

4. The oral care composition according to claim 1, wherein the fluoride ion source is contained in an amount sufficient to supply from 100 to 1000 ppm fluoride ion, based on the total weight of the composition.

5. The oral care composition according to claim 1, rhamnolipid comprises-from 2% by weight to 10% by weight of diRL-C8C10
wherein the weight ratio of the di-rhamnolipids and monorhamnolipids is greater than 98:2.

6. The oral care composition according to claim 1, comprising from 0.1 wt. % to 2 wt. % of the biosurfactant, wherein the composition reduces formation of insoluble complexes of fluoride,
wherein the rhamnolipid comprises from 51% by weight to 95% by weight of diRL-C10C10,
from 0.5% by weight to 3% by weight of monoRL-C10C10, and
from 0.5% by weight to 15% by weight of diRL-C10C12:1, wherein the percentages by weight refer to the sum total of all rhamnolipids present, and
wherein the weight ratio of the di-rhamnolipids and monorhamnolipids is greater than 98:2.

7. The oral care composition according to claim 1, wherein the composition reduces staining of teeth, and wherein the rhamnolipid comprises from 51% by weight to 95% by weight of diRL-C10C10,
from 0.5% by weight to 3% by weight of monoRL-C10C10,
from 0.5% by weight to 15% by weight of diRL-C10C12:1, and
from 0.1% by weight to 25% by weight of diRL-C8C10, where the percentages by weight refer to the sum total of all rhamnolipids present, and
wherein the weight ratio of the di-rhamnolipids and monorhamnolipids is greater than 98:2.

8. The oral care composition according to claim 1, wherein the composition improves deposition/retention of fluoride on teeth, wherein the rhamnolipid comprises
from 51% by weight to 95% by weight of diRL-C10C10,
from 0.5% by weight to 3% by weight of monoRL-C10C10,
from 3% by weight to 12% by weight of diRL-C10C12:1, and
from 2% by weight to 10% by weight of diRL-C8C10, where the percentages by weight refer to the sum total of all rhamnolipids present, and
wherein the weight ratio of the di-rhamnolipids and monorhamnolipids is greater than 97:3.

9. The oral care composition according to claim 2, wherein the fluoride ion source is selected from the group consisting of stannous fluoride, sodium fluoride, potassium fluoride, potassium monofluorophosphate, sodium monofluorophosphate, ammonium monofluorophosphate, sodium fluorosilicate, ammonium fluorosilicate, amine fluorides such as olaflur N'-octadecyltrimethylendiamine-N,N,N'-tris (2-ethanol)-dihydrofluoride and ammonium fluoride.

10. The oral care composition according to claim 2, wherein the fluoride ion source is contained in an amount sufficient to supply from 200 to 500 ppm fluoride ion, based on the total weight of the composition.

11. The oral care composition according to claim 2, wherein the biosurfactant is contained in an amount from 0.1 wt. % to 50 wt. %, based on the total weight of the composition.

12. The oral care composition according to claim 3, wherein the fluoride ion source is contained in an amount sufficient to supply from 200 to 500 ppm fluoride ion, based on the total weight of the composition.

13. The oral care composition according to claim 3, wherein the biosurfactant is contained in an amount from 0.1 wt. % to 50 wt. %, based on the total weight of the composition.

14. The oral care composition according to claim 4, wherein the biosurfactant is contained in an amount from 0.1 wt. % to 50 wt. %, based on the total weight of the composition.

15. The oral care composition according to claim 2, comprising from 0.1 wt. % to 2 wt. % of the rhamnolipid and wherein the fluoride ion source is contained in an amount sufficient to supply from 500 to 1500 ppm fluoride ion.

16. The oral care composition according to claim 5, wherein the biosurfactant wherein the composition reduces formation of insoluble complexes of fluoride.

17. The oral care composition according to claim 5, wherein the composition wherein the composition reduces staining of teeth.

18. The oral care composition according to claim 5, wherein the composition wherein the composition improves deposition/retention of fluoride on teeth.

19. The oral care composition according to claim 1, wherein $R^1$ and $R^2$ are selected from the group consisting of pentenyl, heptenyl, nonenyl, undecenyl and tridecenyl and $(CH_2)_o$ where o is from 1 to 23.

20. The oral care composition according to claim 5, wherein $R^1$ and $R^2$ are selected from the group consisting of pentenyl, heptenyl, nonenyl, undecenyl and tridecenyl and $(CH_2)_o$ where o is from 4 to 12.

* * * * *